(12) United States Patent
Hug et al.

(10) Patent No.: US 8,395,770 B1
(45) Date of Patent: *Mar. 12, 2013

(54) SPECTROSCOPIC CHEMICAL ANALYSIS METHODS AND APPARATUS

(75) Inventors: William F. Hug, Altadena, CA (US); Ray D. Reid, Glendora, CA (US); Rohit Bhartia, Pasadena, CA (US)

(73) Assignee: Photon Systems, Covina, CA (US)

(*) Notice: Subject to any disclaimer, the term of this patent is extended or adjusted under 35 U.S.C. 154(b) by 725 days.

This patent is subject to a terminal disclaimer.

(21) Appl. No.: 12/545,772

(22) Filed: Aug. 21, 2009

Related U.S. Application Data

(63) Continuation-in-part of application No. 12/399,743, filed on Mar. 6, 2009, now Pat. No. 7,800,753, which is a continuation of application No. 11/245,486, filed on Oct. 5, 2005, now Pat. No. 7,525,653.

(60) Provisional application No. 60/616,269, filed on Oct. 5, 2004.

(51) Int. Cl.
*G01J 3/30* (2006.01)

(52) U.S. Cl. ......... 356/317; 356/318; 356/326; 356/417

(58) Field of Classification Search .................. 356/317, 356/318, 301, 326, 417
See application file for complete search history.

(56) References Cited

U.S. PATENT DOCUMENTS

| | | | |
|---|---|---|---|
| 7,564,541 B2* | 7/2009 | Tuschel | 356/73 |
| 7,800,753 B1* | 9/2010 | Hug et al. | 356/317 |
| 7,817,273 B2* | 10/2010 | Bahatt et al. | 356/328 |
| 7,956,991 B2* | 6/2011 | Bangalore et al. | 356/73 |

* cited by examiner

*Primary Examiner* — Layla Lauchman
(74) *Attorney, Agent, or Firm* — Dennis R. Smalley

(57) ABSTRACT

Spectroscopic chemical analysis methods and apparatus are disclosed which employ deep ultraviolet (e.g. in the 200 nm to 300 nm spectral range) electron beam pumped wide bandgap semiconductor lasers, incoherent wide bandgap semiconductor light emitting devices, and hollow cathode metal ion lasers to perform non-contact, non-invasive detection of unknown chemical analytes. These deep ultraviolet sources enable dramatic size, weight and power consumption reductions of chemical analysis instruments. Chemical analysis instruments employed in some embodiments include capillary and gel plane electrophoresis, capillary electrochromatography, high performance liquid chromatography, flow cytometry, flow cells for liquids and aerosols, and surface detection instruments. In some embodiments, Raman spectroscopic detection methods and apparatus use ultra-narrow-band angle tuning filters, acousto-optic tuning filters, and temperature tuned filters to enable ultra-miniature analyzers for chemical identification. In some embodiments Raman analysis is conducted along with photoluminescence spectroscopy (i.e. fluorescence and/or phosphorescence spectroscopy) to provide high levels of sensitivity and specificity in the same instrument.

29 Claims, 13 Drawing Sheets

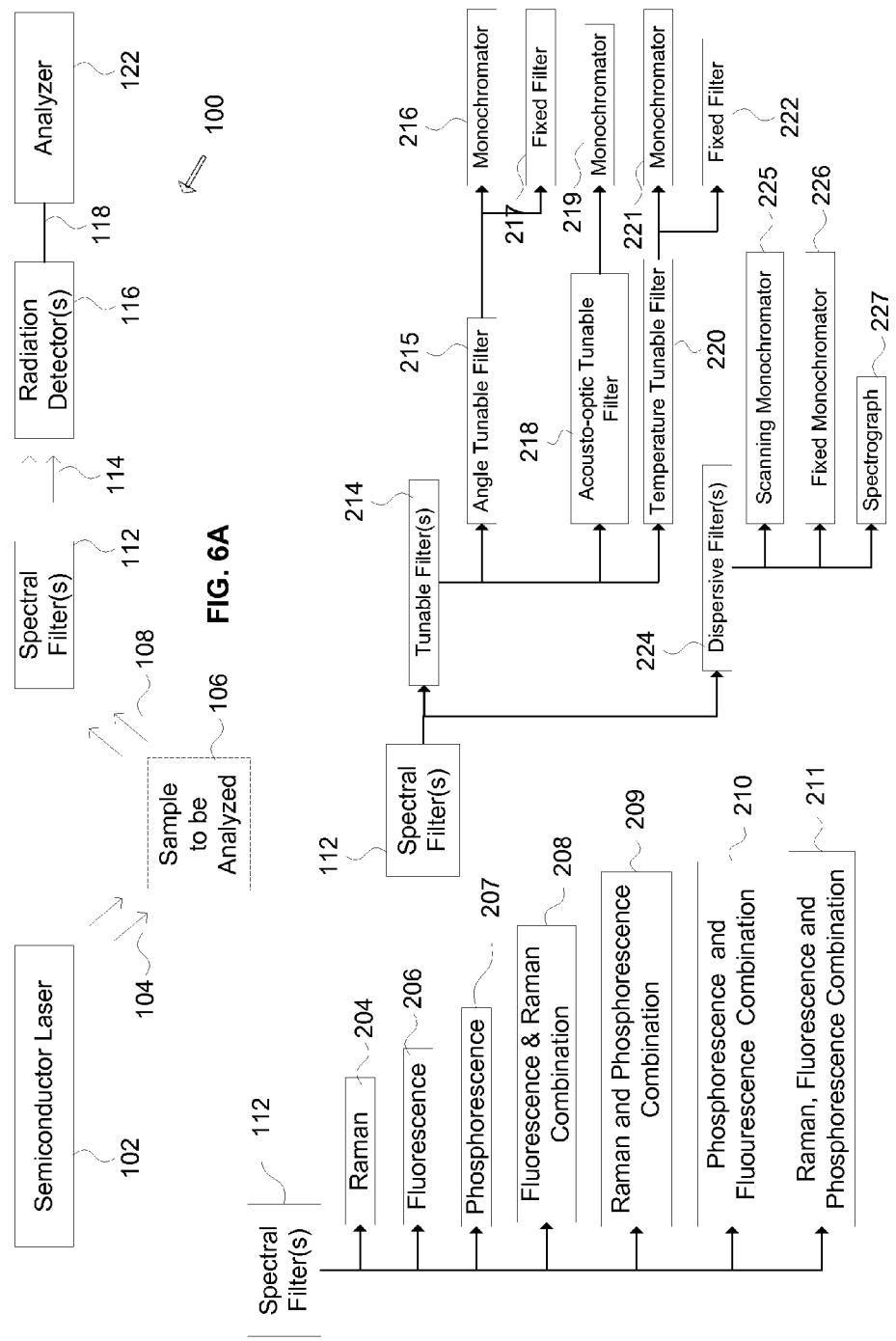

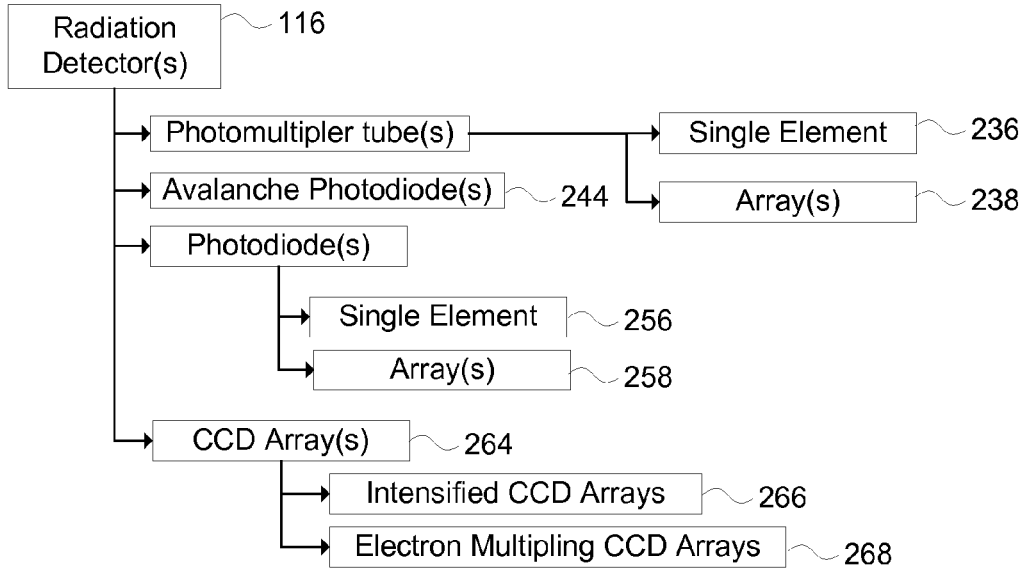
FIG. 6D
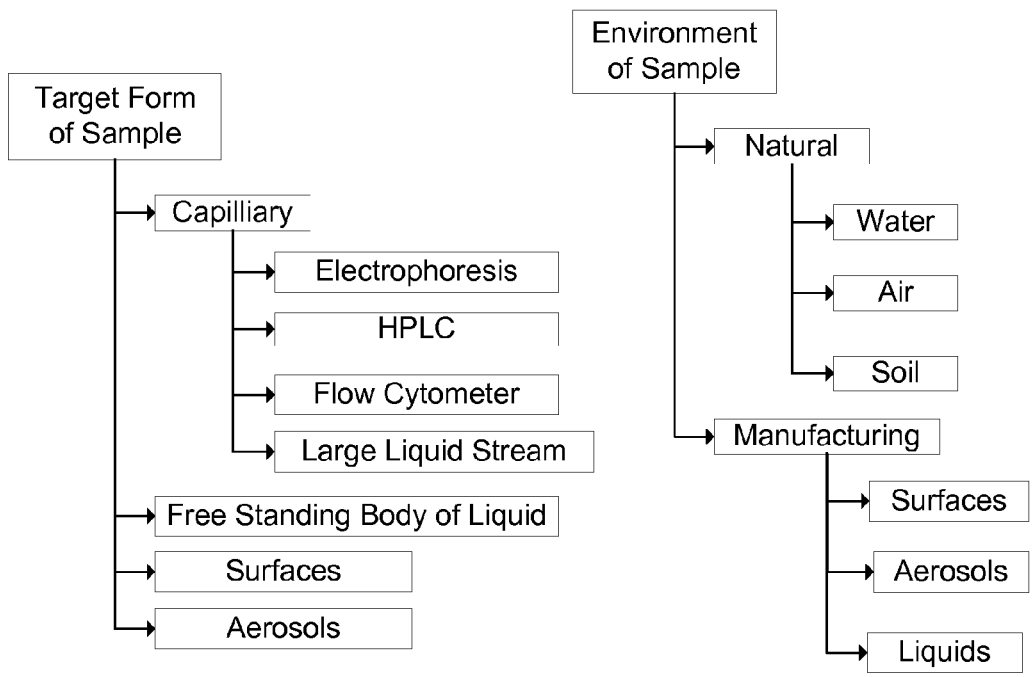
FIG. 6E
FIG. 6F

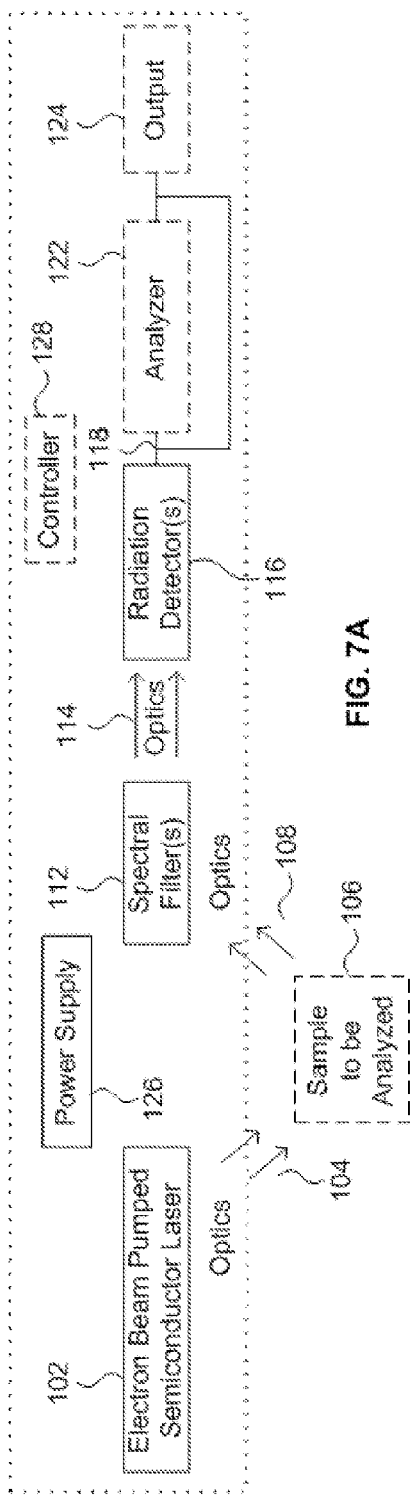
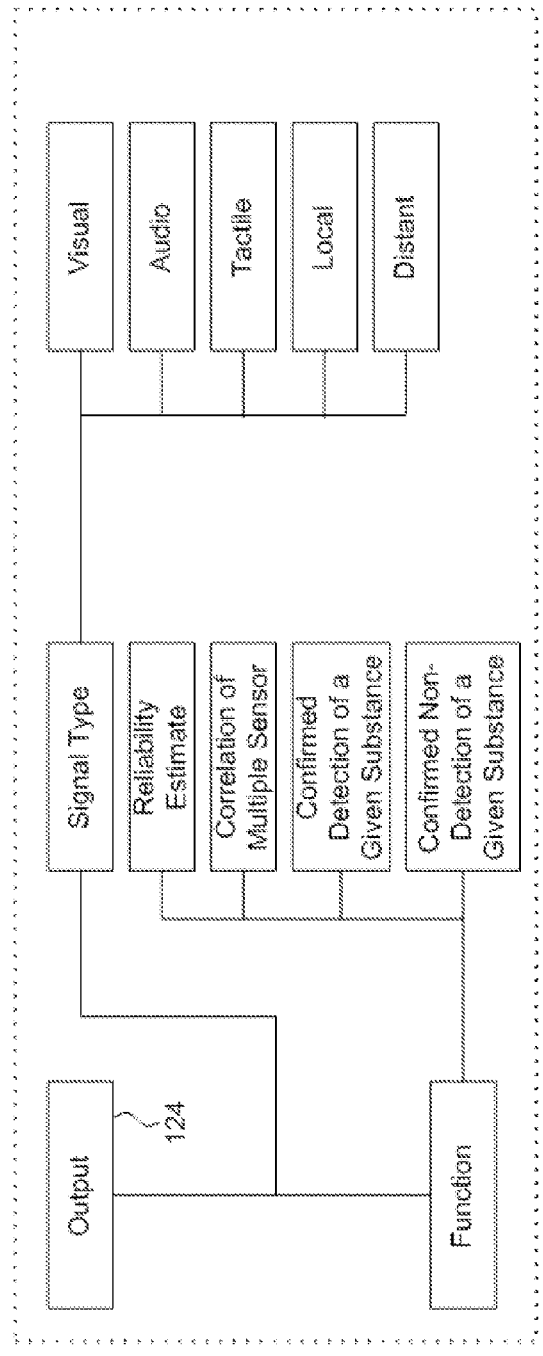

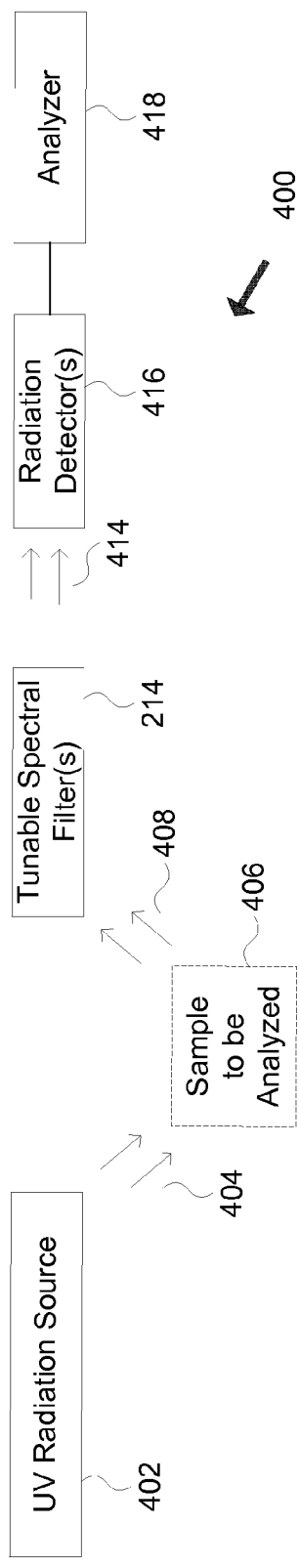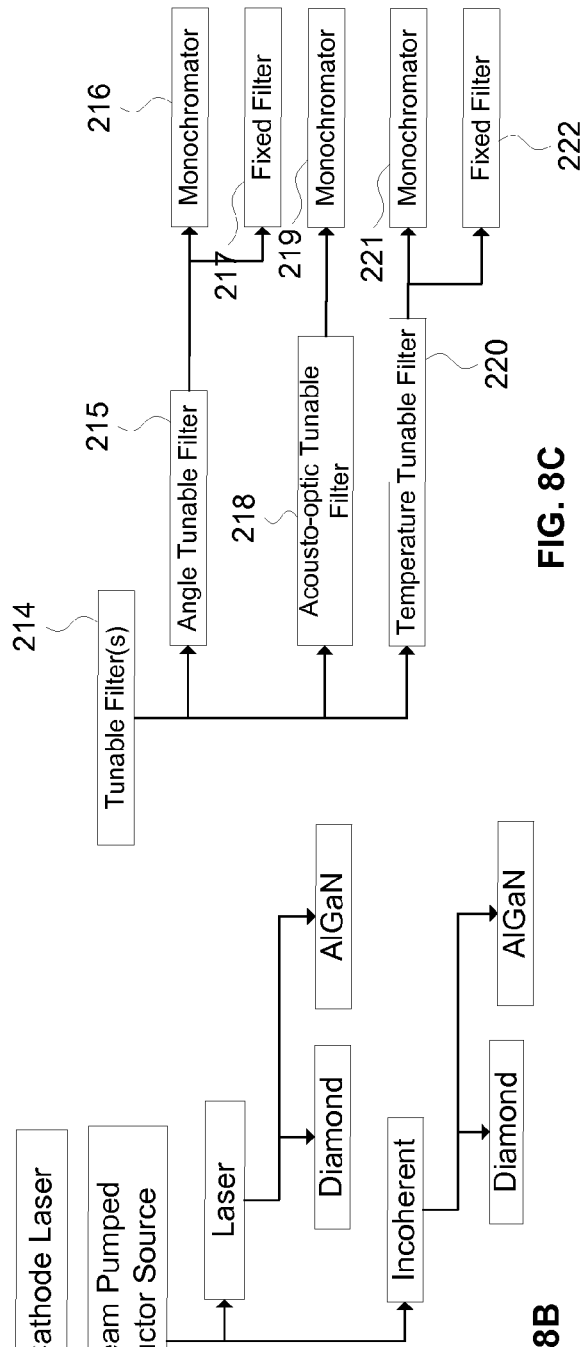

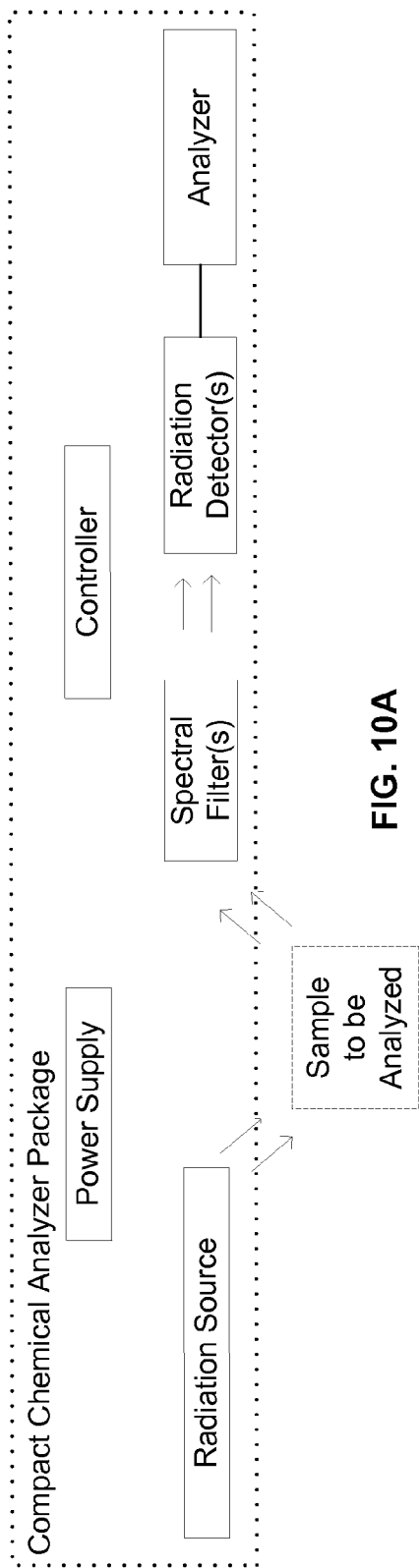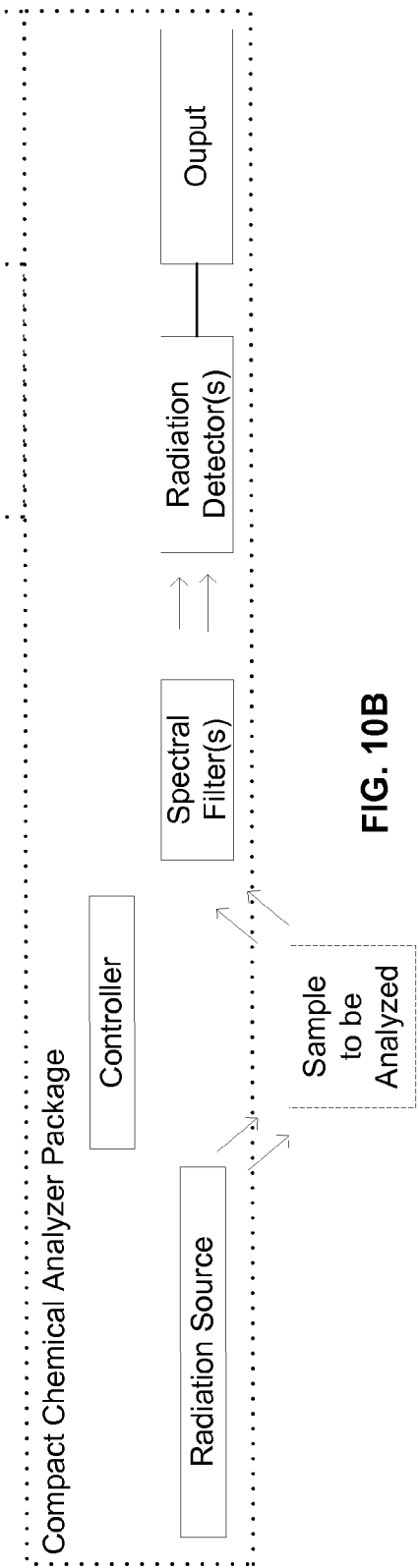

SPECTROSCOPIC CHEMICAL ANALYSIS METHODS AND APPARATUS

RELATED APPLICATIONS

This application is a continuation-in-part of U.S. patent application Ser. No. 12/399,743, filed Mar. 6, 2009 now U.S. Pat. No. 7,800,753 which in turn is a continuation of U.S. patent application Ser. No. 11/245,486 filed Oct. 5, 2005 now U.S. Pat. No. 7,525,653 which in turn claims benefit of U.S. Provisional Application No. 60/616,269, filed Oct. 5, 2004. Each of these applications is incorporated herein by reference as if set forth in full herein.

US GOVERNMENT RIGHTS

The inventions set forth herein were made with U.S. Government support under NASA Contract No. NAS2-02086 and/or under DARPA Contract No. W31 P4Q-04-C—R039. The Government has certain rights to the invention.

FIELD OF THE INVENTION

This invention relates to non-contact spectroscopic methods and apparatus for performing chemical analysis and the ideal wavelengths and sources needed for this analysis. In some embodiments, for example, the method can be used, in a microscope or macroscope to provide measurement of Raman and/or photoluminescence, (i.e. native fluorescence and/or phosphorescence) emission spectra and/or decay time characteristics either by point-by-point measurement or by global imaging of emissions and decay times within specific ultraviolet spectral bands. In other embodiments, the method can be used in analytical instruments such as capillary electrophoresis, capillary electrochromatography, high performance liquid chromatography, flow cytometry, and related instruments for detection and identification of unknown analytes using a combination of photoluminescence (i.e. native fluorescence and/or phosphorescence) and/or Raman spectroscopic methods. Further embodiments of this invention use deep ultraviolet sources of radiation generated by electron-beam-pumped, wide bandgap, semiconductor devices, that include, for example alloys and structures made from aluminum and gallium nitrides, diamond, or related materials.

BACKGROUND OF THE INVENTION

The use of optical sources of radiation such as lasers, light emitting diodes (LED's), arc lamps, and other sources of incoherent radiation to perform chemical analysis and identification has been known for many years and such sources have been used in a wide range of chemical analysis and analytical instruments. Among these instruments, capillary electrophoresis, high performance liquid chromatography, flow cytometry, Raman and fluorescence microscopy and spectroscopy are emerging as powerful analytical tools for a wide range of biological and chemical research, as well as clinical, industrial, and governmental applications. These instrumental techniques are being increasingly used in commercial and governmental applications such as product inspection during the manufacture of pharmaceutical and medical products, manufactured food and chemical products, environmental testing, and other applications.

When a sample is exposed to radiation (e.g. infrared (IR) radiation, visible light, or ultraviolet (UV) radiation) at a given frequency, some of the radiation is transmitted through the sample. Some of the radiation is elastically scattered and retains the same frequency as the incident radiation. Some of the radiation is absorbed in the sample. The absorbed radiation is either re-emitted after interaction with the sample or converted to thermal energy in the sample. The re-emitted radiation is sometimes referred to as inelastically scattered radiation. The inelastically scattered radiation is re-emitted as fluorescence or phosphorescence at wavelengths longer than, or frequencies shorter than the irradiation frequency, and a small fraction is re-emitted as Raman scattered radiation. Fluorescence or phosphorescence emissions are red shifted from the excitation frequency and have a spectral distribution that is relatively independent of the excitation frequency. Raman emissions are dependent on excitation frequency and are measured as a sum or difference frequency from the excitation frequency. Absorption of radiation requires that the energy of the exciting photon is higher than the first excited state of the molecule being excited. Raman emissions can be either blue (anti-Stokes) or red (Stokes) shifted from the excitation frequency by an amount determined by the rotational and vibrational bonds within the molecules being irradiated. Raman scattering efficiency is typically very low compared to fluorescence. However, when the energy of the excitation radiation corresponds to strong absorption bands of the analyte, a resonance effect can amplify the Raman signal by many orders of magnitude.

Fluorescence, phosphorescence and Raman techniques are employed for chemical detection and identification in a wide range of instruments. Lasers, LED's and other sources are typically used for excitation. Chemical separation technologies such as capillary electrophoresis (CE), high performance liquid chromatography (HPLC), capillary electrochromatography (CEC), and various related instrumental forms allow rapid separation of complex chemical and biochemical mixtures into component elements. Laser induced fluorescence (LIF) allows the sensitive detection of separated elements or analytes where limits of detection have been demonstrated into the zeptomole range.

A major drawback to the use of fluorescence detection is that the vast majority of chemicals do not absorb strongly at visible or infrared wavelengths where simple, inexpensive lasers emit. In order to match the emission wavelength of these desirable lasers and other sources, fluorescence detection performed above about 300 nm requires derivatization of most analytes with a fluorescent dye tag prior to analysis. This is highly inconvenient, especially at low analyte concentrations, and for compounds that lack appropriate functional groups. For multifunctional compounds such as proteins, it is very difficult to ensure stoichiometrical reactions that can result in complex mixtures after derivatization. Derivatization limits the types of molecules that can be studied, can lower overall detection sensitivity, reduces the ability to find unexpected analytes in complex mixtures, and may alter the very chemistry being studied. Derivatization is commonly employed in analytical instruments today because of the lack of suitable lasers in the deep UV with small size, reasonable power consumption, and acceptable cost. The sensitivity and specificity as well as simplicity and ease of use of analytical instruments have been demonstrated to be considerably enhanced when combined with a laser that emits in the deep UV between 200 nm and 300 nm. These advantages were demonstrated using lasers that are unacceptable in a commercial instrument application because of their size, weight, power consumption, and/or cost. The advantages of deep UV excitation are true for detection in chemical separation instruments as well as in point-by-point or global imaging instruments, and other instruments using optical methods of detection. In addition to fluorescence, Raman spectroscopy is a powerful analytical method for determining properties of unknown materials. Narrow Raman emission bands carry a great deal more information on molecular structure, in contrast to broadband fluorescence emission. It has been hampered as an analytical method by the fact that normal Raman scatter cross-sections of materials are typically very small. Another problem that has hampered Raman spectroscopy as an analytical method is fluorescence background from many materials at wavelengths of interest in obtaining Raman spectra. In the visible portion of the spectrum where many types of lasers are available, many materials emit fluorescence that overwhelms the small Raman emissions from a sample. To alleviate this problem instruments have been developed which operate in the near infrared where fluorescence background is greatly diminished or, in some cases, eliminated. The problem remains that Raman scatter cross-sections in the infrared are small and powerful lasers are needed to obtain Raman spectral data. In addition to their other problems, these powerful lasers sometimes cause sample damage.

Several advantages arise for Raman spectroscopy and analysis when using a deep ultraviolet laser to irradiate a sample. First, scatter cross-sections are inversely proportional to the fourth power of excitation wavelength. Thus, as the excitation wavelength of a laser is moved from the near infrared to the ultraviolet, an increase over 100 times in Raman scattering typically occurs. Second, when excitation occurs below about 250 nm, fluorescence background is eliminated within the Raman spectral range of most samples. This ubiquitous fluorescence, which is a major impediment for visible wavelength Raman studies, does not occur for UV spectral studies below about 270 nm. This is because at these high energies the excited state of most molecules in a condensed phase relaxes by means of fast radiationless processes before it has time to fluoresce. Third, when excitation occurs within an electronic absorption band of the sample, a resonance effect causes dramatic increases in Raman signal strength, often over one million to one hundred million times, thus eliminating the need for powerful lasers. Many types of materials have strong absorption bands in the deep ultraviolet below about 300 nm. These include organic and biological materials as well as a large range of other materials. And fourth, resonance Raman bands are enhanced preferentially for those molecular bonds associated with the electronic absorption, thus considerably simplifying the Raman spectra and making them more easily interpreted. For these types of samples, deep ultraviolet Raman spectroscopy and single band Raman imaging can be important analytical methods.

The state of the art of Raman spectroscopy can still be advanced by the application of additional deep UV laser sources to such analytic instruments (particularly low power and/or small size sources), by using optical components that allow further reductions in system size, weight, power consumption, and the like.

Various analytic instruments and analytic methods have been described previously. Patents having such teachings include:
1. U.S. Pat. No. 6,287,869, entitled "Analytic Instrument Using a Sputtering Metal Ion Laser" by Hug, et al.;
2. U.S. Pat. No. 6,002,476, entitled "Chemical Imaging System" by Treado;
3. U.S. Pat. No. 5,623,342, entitled "Raman Microscope" by Batchelder, et. al.;
4. U.S. Pat. No. 5,442,438, entitled "Spectroscopic Apparatus and Methods", by Batchelder, et. al.; and
5 U.S. Pat. No. 5,194,912, entitled "Raman Analysis Apparatus" by Batchelder, et. al.

The teachings of each of these patents are hereby incorporated herein by reference as if set forth in full. With the exception of the '869 patent, a feature that universally distinguishes these patents from some embodiments of the invention is that they are related to apparatus utilizing visible or infrared wavelengths. The teachings of the '869 patent will be discussed further herein after.

Additional publications providing teachings about analytic instruments and methods include:
1. Ianoul, A., T. Coleman, and S. A. Asher, "UV Resonance Raman Spectroscopic Detection of Nitrate and Nitrite in Wastewater Treatment Processes", *Anal. Chem., Vol.* 74, pp. 1458-1461, 2002.
2. Storrie-Lombardi, M. C., W. F. Hug, G. D. McDonald, A. I. Tsapin, and K. H. Nealson. "Hollow cathode ion laser for deep ultraviolet Raman spectroscopy and fluorescence imaging". *Rev. Sci. Instruments,* 12, 4452-4459, December 2001
3. Sparrow, M. C., J. F. Jackovitz, C. H. Munro, W. F. Hug, and S. A. Asher, "A New 224 nm Hollow Cathode UV Laser Raman Spectrometer", *J. App. Spectroscopy*, Vol. 55, No. 1, January 2001.
4. Gillespie, S. R. and J. W. Carnahan, "Ultraviolet Quartz Acousto-optic Tunable Filter Wavelength Selection for Inductively Coupled Plasma Atomic Emission Spectrometry", *J. App. Spectroscopy*, Vol. 55, No. 6, 2001.
5. Wu, Q, T. Hamilton, W. H. Nelson, S. Elliott, J. F. Sperry, and M. Wu, "UV Raman Spectral Intensities of *E. Coli* and Other Bacteria Excited at 228.9, 244.0 and 248.2 nm", *Anal. Chem.* Vol. 73, No. 14, pp. 3432-3440, Jul. 15, 2001.
6. McCreery, R. L., "Raman Spectrocopy for Chemical Analysis", John Wiley & Sons, ISBN #0-471-25287-5, 2000.
7. Munro, C. H., V. Pajcini, and S. A. Asher, "Dielectric Stack Filters for Ex Situ and In Situ UV Optical-Fiber Probe Raman Spectroscopic Measurements", *App. Spect.*, Vol. 51, No. 11, pp 1722-1729, 1997.
8. Morris, H., C. et. al., "Liquid Crystal Tunable Filter Raman Chemical Imaging", *App. Spect.*, Vol. 50, No. 6, pp. 805-811, 1996.
9. Turrell, G, et. al., "Raman Microscopy", Academic Press Ltd., ISBN#0-12-189690-0, 1996.
10. Macleod, A., "Thin-Film Optical Filters", McGraw-Hill, ISBN#0-07-044694-6, reprinted 1989
11. Treado, P. J., and M. D. Morris, "A Thousand Points of Light: The Hadamard Transform in Chemical Analysis and Instrumentation", *Anal. Chem.*, Vol 61, No. 11, pp. 722-734, Jun. 1, 1989.
12. Asher, S. A., "Raman Spectroscopy of a Coal Liquid Shows That Fluorescence Interference Is Minimized with Ultraviolet Excitation", *Science*, Vol. 225, 20 Jul. 1984.
13. Wolf, W. L. ed., Handbook of Military Infrared Technology, Office of Naval Research, Dept. of the Navy, Washington, D.C., pp. 286-306, 1965.
14. Military Standardization Handbook, MIL-HDBK-141, Section 20, 5 Oct. 1962. (angle dependence, p. 20-11)
15. Jenkins, F. A. and H. E. White, *Fundamentals of Optics*, (McGraw Hill), 1957.
16. Mooney, C. F., and A. F. Turner, "Infrared Transmitting Interference Filters, Proceedings of the Conference on Infrared Optical Materials, Filters, and Films", Engineering Research and Development Laboratories, Fort Belvoir, Va. (1955).

Each of the publications is hereby incorporated herein by reference as if set forth in full. Additional references having such teachings are found in the background of previously incorporated U.S. Pat. No. 6,287,869. These additional references are hereby incorporated therein by reference as if set forth in full.

The teachings in U.S. Pat. No. 6,287,869 provided improved and more commercially viable analytical systems by providing deep UV radiation sources in the form of sputtering metal ion hollow cathode lasers for use in such systems. These lasers provided improved choice of emission wavelengths, improved duty cycle, reduced size, reduced power consumption, reduced complexity, reduced cost and improved reliability. A need remains, however, for other UV radiation sources that provide further size reductions, weight reductions and cost savings for use in analytical instruments.

Semiconductor optical sources including lasers and light emitting diodes may be the ultimate forms of radiation sources for analytical instruments since they typically are very small, have low power consumption and can be produced at low cost. Research on blue and ultraviolet lasers has been ongoing for many years with significant progress. But several major technical roadblocks have impeded progress in demonstrating sources which operate in the deep UV, especially at wavelengths less than about 300 nm. Wide bandgap semiconductor materials based on alloys of aluminum and gallium nitrides plus various dopants are being extensively investigated to fulfill the need for UV semiconductor sources. Pure aluminum nitride (AlN) has a bandgap of 6.2 electron volts (eV), which corresponds to an emission wavelength of 200 nm. Pure gallium nitride (GaN) has a bandgap of 3.4 electron volts, which corresponds to an emission wavelength of 365 nm. By alloying these materials any emission wavelength between 200 nm and 365 nm can theoretically be produced. To produce a semiconductor laser with emission wavelength less than 250 nm requires an aluminum mole fraction in the alloy greater than about 60%. The major roadblocks to producing deep UV semiconductor sources have been:

1. the inability to adequately p-dope AlGaN materials with aluminum content greater than a few percent (i.e. measure as mole fraction);
2. the inability to make low resistance, ohmic, contacts to AlGaN alloys with aluminum content greater than a few percent;
3. Lattice mismatch with available substrate materials resulting in high defect density in active region;
4. Inability to form facets with low losses at deep UV wavelengths; and
5. Difficulty in forming waveguiding layers in high Al-content AlGaN alloys.

A need exists in the art for overcoming these roadblocks. The first two items above are the most significant of these roadblocks.

The general idea of using electron beams to pump various materials to produce laser output is not new. In fact, a significant amount of literature and some patents exist on various devices and applications based on these methods. These publications date back to 1964. These publications include the following articles and patents, each of which is incorporated herein by reference:

1. C. E. Hurwitz and R. J. Keyes, "Electron-beam-pumped GaAs Laser", App. Phys. Lett, Vol. 5, No. 7, pp. 139-141, (Oct. 1, 1964).
2. C. E. Hurwitz, "Efficient ultraviolet laser emission in e-beam excited ZnS", Appl.Phys.Lett., v.9, N.3, pp 116-118 (1966)
3. C. E. Hurwitz, High Power and Efficiency in CdS Electron Beam Pumped Lasers, Applied Physics Letters, vol. 9, No. 12, Dec. 15, 1966, pp. 420-423.
4. C. E. Hurwitz, "Electron-beam pumped lasers of CdSe and CdS", App. Phys. Lett., Vol. 8, No. 5, pp. 121-124, (March 1966)
5. C. E. Hurwitz, "Efficient visible lasers of CdSeSe by electron-beam-excitation", Applied Physics Letters 8, 243 (1966)].
6. C. A. Klein, "Further remarks on electron beam pumping of laser materials", Appl.Optics, 5, 12, 1922 (1966)
7. Nasibov et al., "Electron-Beam Tube with a Laser Screen", Sov. J. Quant. Electron., vol. 4, No. 3, September 1974, pp. 296-300.
8. O. V. Bogdankevich et al., Application of Electron Beam Pumped Semiconductor Lasers to Projection Television, IEEE Journal of Quantum Electronics, vol. 13, No. 9 (September 1977), p. 65D.
9. O. V. Bogdankevich, The Use of Electron-Beam Pumped Semiconductor Lasers in Projection Television, IEEE Journal of Quantum Electronics, vol. QE-14, No. 2, February 1978, pp. 133-135.
10. Bogdankevich et al., "Multilayer GaAs-AlAs Heterostructure Laser Pumped Transversely by an Electron Beam", Sov. J. Quantum Electron. 10 (6), June 1980, pp. 693-695.
11. Bogdankevich et al., "Influence of Doping of Ga.sub.0.68 Al.sub.0.32 As on its Cathodoluminescence and Threshold Current Density of a Laser Pumped by an Electron Beam", Sov. J. Quant. Electron., 11 (1), January 1981, pp. 119-121.
12. B. Kozlovskii, A. Nasibov, et.al., Sov. J. Quant. Electr., 12, 505 (1982)
13. E. Markov, V. Smirnov, V. Khryapov, "Physics and technical application AB Semiconductors", V Conf., Prod., Vilnius, SU, 3, 131 (1983)
14. O. V. Bogdankevich et al., Distribution of the excitation density in electron-beam-pumped semiconductor lasers, Sov. J. Quantum Electron. 13 (11), November 1983, pp. 1453-1459.
15. Tong, F., R. M. Osgood, A. Sanchez, and V. Daneu, "Electron-beam-pumped two-dimensional laser array with tilted mirror resonator", App.Phys.Letters (ISSN00003-6951) Vol. 52, pp. 1303-1305, Apr. 18, 1988
16. I. Akimova, V. Kozlovskii, et. al, "The influence of stoichiometry in A2B6 monocrystal compounds on the characteristics of a semiconductor electron-beam pumped laser", Proc. Of Lebedev Phys. Inst., Nova Science Publ., USA, v.177, pp. 195-233, 1988.
17. A. Nasibov, V. Kozlovsky, Y. Skasyrsky, "Deep blue and ultraviolet e-beam pumped semiconductor lasers", SPIE Vol. 1041, Metal Vapor Deep Blue and Ultraviolet Lasers, Los Angeles, Calif., 17-20 Jan. 1989.
18. Molva, E., R. Accomo, G. Labrunie, J. Cibert, C. Bodin, Le Si Dang, and G. Feuillet, "Microgun-pumped semiconductor laser", App.Phys.Letters, Vol. 62(8), pp. 796-798, Feb. 22, 1993
19. O. V. Bogdankevich, "Electron-beam-pumped semiconductor lasers", Quantum Electronics, Vol 24, No. 12, pp. 1031-1053, 1994.
20. D. Nerve, R. Accomo, E. Molva, L. Vanzetti, J. J. Paggel, L. Sorba, and A. Francoisi, "Microgun-pumped blue lasers", App. Phys. Letters, Vol. 67(15), pp. 2144-2146, Oct. 9, 1995
21. V. I. Kozlovshy, A. B. Krysa, Y. K. Skyasyrsky, Y. M. Popov, w.S.DenBaars, "Electron beam pumped MQW InGaN/GaN laser", MRS Internet J. Nitride Semicond.Res.2, 38 (1997).

22. J. M. Bonard, J. D. Ganiere, L. Vanzetti, et. al., "Transmission electron microscopy and cathodoluminescence studies of extended defects in electron-beam-pumped $Zn_{1-x}Cd_xSe/ZnSe$ blue-green lasers", J. App. Phys., (83) 4 p1945 (15 Feb. 1998)

23. S. Krivoshlykov, "Compact high-efficiency electron-beam-pumped semiconductor laser operating at room temperature", BMDO Phase I SBIR 1999

24. Nicholls, J. E., B. Lunn, et.al., "Electron-beam-pumped near-UV semiconductor laser emission", EPSRC reference number GR/L27206, University of Hull, UK.

25. J. R. Packard, et. al., "Electron Beam Laser", U.S. Pat. No. 3,757,250, Sep. 4, 1973

26. R. R. Rice, et.al., "Vertical cavity electron beam pumped semiconductor lasers and methods", U.S. Pat. No. 5,807,764, Sep. 15, 1998

27. R. R. Rice, et.al., "Vertical cavity electron beam pumped semiconductor lasers and methods", U.S. Pat. No. 5,677,923, Oct. 14, 1997.

28. D. A. Campbell, et.al., "Zinc Oxide Laser", U.S. Pat. No. 3,505,613, Apr. 7, 1970.

A need exist in the field for extending the use of electron beam pumping to additional materials and applications so as to enable improved radiation sources (e.g. lasers and incoherent sources) which in turn may enable improved applications for such sources, e.g. improved chemical analysis methods and devices.

SUMMARY OF THE INVENTION

It is an object of some embodiments of the invention to provide an improved Raman analysis method and/or an improved photoluminescence analysis method (i.e. an improved native fluorescence analysis method, and/or an improved phosphorescence analysis method).

It is an object of some embodiments of the invention to provide an analytic method or apparatus requiring or having reduced size (e.g. a size under 20 liters).

It is an object of some embodiments of the invention to provide an analytic method or apparatus requiring or having reduced weight (e.g. a weight under 100 pounds).

It is an object of some embodiments of the invention to provide an analytic method or apparatus requiring or having reduced power consumption (e.g. power consumption under 100 watts).

It is an object of some embodiments of the invention to provide an electron-beam-pumped semiconductor radiation producing method or source that can emit at a wavelength or wavelengths below 300 nm, e.g. in the deep ultraviolet between about 200 nm and 300 nm, and more preferably less than about 260 nm. In some variations of this objective the method or source is to produce incoherent radiation while in other implementations it produces laser radiation. In some variations, this object is achieved, for example, using a aluminum gallium nitride (ALGaN) emission medium while in other implementations a diamond emission medium may be used It is an object of some embodiments of the invention to provide an analytic method or instrument that irradiates a sample with deep UV radiation and uses an improved filter for separating wavelengths to be detected.

It is an object of some embodiments of the invention to provide a method or apparatus that provides multi-stage analysis of a sample where the stages may be separated by different wavelength ranges, detection of different types of inelastically scattered radiation (e.g. Raman, fluorescence, phosphorescence), and/or detection at different times relative to application of excitation radiation.

Other objects and advantages of various aspects of the invention will be apparent to those of skill in the art upon review of the teachings herein. The various aspects of the invention, set forth explicitly herein or otherwise ascertained from the teachings herein, may address any one of the above objects alone or in combination, or alternatively may address some other object of the invention ascertained from the teachings herein. It is not intended that any specific aspect of the invention (that is explicitly set forth below or that is ascertained from the teachings herein) necessarily address any of the objects set forth above let alone address all of these objects simultaneously, but some aspects may address one or more of these objects or even all of these objects simultaneously.

In a first aspect of the invention a method of providing a chemical analysis of a sample includes: supplying a sample to be analyzed; applying excitation radiation from a semiconductor source having a wavelength less than about 300 nm directly or indirectly onto the sample; receiving emission radiation, directly or indirectly, from the sample at a spectral filter which is capable of passing a selected range of wavelengths of the emission radiation along a given optical path; measuring an amount of the selected emission radiation present, using a detector located directly or indirectly along the selected optical path; correlating information concerning the amount of selected emission radiation measured by the detector with data associated with one or more chemical compounds of interest to provide at least a partial chemical analysis of the sample.

In a second aspect of the invention a method of providing a chemical analysis of a sample includes: supplying a sample to be analyzed; applying radiation from an electron beam pumped semiconductor light emitting device directly or indirectly onto the sample; receiving emission radiation, directly or indirectly, from the sample at a spectral filter which is capable of passing a selected range of wavelengths of the emission radiation along a given optical path; measuring an amount of the selected emission radiation present, using a detector located directly or indirectly along the selected optical path; and correlating information concerning the amount of selected emission radiation measured by the detector with data associated with one or more chemical compounds of interest to provide at least a partial chemical analysis of the sample.

In a third aspect of the invention a method of providing integrated chemical analysis of a sample includes: supplying a sample to be analyzed; applying excitation radiation directly or indirectly onto the sample; receiving emission radiation, directly or indirectly, from the sample at a $1^{st}$ spectral filter which is capable of passing a $1^{st}$ selected emission radiation along a $1^{st}$ optical path; receiving emission radiation, directly or indirectly, from the sample at a $2^{nd}$ spectral filter which is capable of passing a $2^{nd}$ selected emission radiation along a $2^{nd}$ optical path; measuring an amount of the $1^{st}$ selected emission radiation present using a $1^{st}$ detector located directly or indirectly along the $1^{st}$ optical path; correlating information concerning the amount of selected emission radiation measured by the $1^{st}$ detector with data associated with one or more chemical compounds of interest to provide at least a partial $1^{st}$ chemical analysis of the sample; measuring an amount of the $2^{nd}$ selected emission radiation using a $2^{nd}$ detector located directly or indirectly along the $2^{nd}$ optical path; and correlating information concerning the amount of $2^{nd}$ selected emission radiation measured by the $2^{nd}$ detector with data associated with one or more chemical compounds of interest to provide at least a partial $2^{nd}$ chemical analysis of the sample.

In a fourth aspect of the invention a method of providing a chemical analysis of a sample, includes: supplying a sample to be analyzed, applying UV laser radiation directly or indirectly onto the sample; receiving radiation, directly or indirectly, from the sample at a tunable spectral filter which is capable of passing a selected radiation along a given optical path; measuring an amount of the selected radiation present using a detector located directly or indirectly along the selected optical path; and correlating information concerning the amount of radiation measured by the detector with data associated with one or more chemical compounds of interest to provide at least a partial chemical analysis of the sample.

In a fifth aspect of the invention a method of providing a chemical analysis of a sample, includes: (a) supplying a sample to be analyzed; (b) applying ultraviolet excitation radiation from a source directly or indirectly onto the sample to produce emission radiation in the form of Raman emission radiation within a first range of wavelengths and photoluminescence emission radiation within a second range of wavelengths; (c) receiving the emission radiation, directly or indirectly, from the sample at at least one first spectral filter which is capable of passing the Raman emission radiation within at least a portion of the first range of wavelengths along a first optical path; (d) receiving the emission radiation, directly or indirectly, from the sample at at least one second spectral filter which is capable of passing the photoluminescence emission radiation within at least a portion of the second range of wavelengths along a second optical path; (e) measuring an amount of the Raman emission radiation using at least one first detector located directly or indirectly along the first optical path; (f) measuring an amount of the photoluminescence emission radiation using at least one second detector located directly or indirectly along the second optical path; and (g) correlating information concerning the amounts of the Raman emission radiation and photoluminescence emission radiation measured by the at least one first detector and the at least one second detector, respectively, with data associated with one or more chemical compounds of interest to provide at least a partial chemical analysis of the sample.

Numerous variations of the fifth aspect of the invention are possible and include, for example, one or more of: (1) the photoluminescence emission radiation including fluorescence emission radiation, phosphorescence emission radiation, or both; (2) measuring the fluorescence and phosphorescence emission radiation at different times when both are in the photoluminescence emission radiation; (3) the source being selected from the group consisting of: (a) a semiconductor source, (b) a an electron beam pumped semiconductor laser; (c) an electron beam pumped incoherent semiconductor source; and (d) an electron beam pumped AlGaN source; and (e) a hollow cathode laser; (4).the excitation radiation having a wavelength selected from the group consisting of (a) a wavelength less than 300 nm and (b) a wavelength less than about 250 nm; .(5) at least one of the at least one first spectral filter or at least one second spectral filter including a selected filter chosen from the group consisting of (a) a tunable filter; (b) a dispersive device; an acousto-optic tunable filter; a temperature tunable filter; . (6) the chemical analysis being performed in conjunction with one or more sample handling or separation methods selected from the group consisting of: (a) capillary electrophoresis (CE), (b) capillary electrochromatography (CEC), (c) high performance liquid chromatography (HPLC), (d) microcapillary HPLC, (e) flow cytometry, (f) liquid flow cell methods, (g) air flow cell methods, and (h) a surface detection method; .(7) the selected filter of the fifth variation of the fifth aspect of the invention including an angle tunable filter wherein the orientation of the angle tunable filter, with respect to received emission radiation, is adjustable so as to enable the Raman emission radiation or the photoluminescence radiation that reaches the at least one first detector or the at least one second detector, respectively, to vary in wavelength and optionally wherein the receiving and measuring operations occur multiple times with the at least one tunable filter tuned to different wavelengths so as to obtain data for a plurality of measurements for a plurality of wavelengths, wherein the correlating comprises determining relative amounts of the measurements for at least two different wavelengths of the plurality of wavelengths and comparing the relative amounts with the data; .(8) the measuring of the amount of the Raman emission radiation and the measuring of the amount of the photoluminescence emission radiation occur simultaneously; (9).the measuring of the amount of the Raman emission radiation and measuring of the amount of the photoluminescence emission radiation occur at different times; and/or (10) the measuring of the amount of an emission radiation selected from the group consisting of the Raman emission radiation and the photoluminescence emission radiation is repeated multiple times and optionally at least one of the repeated measurings occur after irradiation of the sample has ended. Further variations are also possible and include various mixtures of the above noted variations so long as such mixtures maintain the functionality of the method as a whole.

In a sixth aspect of the invention a method of providing a chemical analysis of a sample, includes: (a) supplying a sample to be analyzed; (b) applying ultraviolet excitation radiation from a source directly or indirectly onto the sample to produce emission radiation in the form of photoluminescence emission radiation within a first range of wavelengths; (c) receiving the emission radiation, directly or indirectly, from the sample at at least one first spectral filter which is capable of passing the photoluminescence emission radiation within at least a portion of the first range of wavelengths along a first optical path; (d) measuring an amount of the photoluminescence emission radiation using at least one first detector located directly or indirectly along the first optical path; and (e) correlating information concerning the amounts of the photoluminescence emission radiation measured by the at least one first detector with data associated with one or more chemical compounds of interest to provide at least a partial chemical analysis of the sample.

Numerous variations of the sixth aspect of the invention are possible and include, for example, one or more of: (1) the photoluminescence emission radiation including fluorescence emission radiation; (2) the photoluminescence emission radiation including phosphorescence emission radiation; (3) the photoluminescence emission radiation including both fluorescence and phosphorescence emission radiation which are each measured by the at least one first detector at difference times; (4) the additional steps of .(f) receiving photoluminescence emission radiation, directly or indirectly, from the sample at at least one second spectral filter which is capable of passing photoluminescence emission radiation within a second range of wavelengths, which is different from the first range of wavelengths, along a second optical path; (g) measuring an amount of the photoluminescence emission radiation within the second range of wavelengths using at least one second detector located directly or indirectly along the second optical path; and (h) correlating information concerning the amount of photoluminescence emission radiation within the second range of wavelengths measured by the at least one second detector with data associated with one or more chemical compounds of interest to provide at least partial chemical analysis of the sample; (5) the at least portion of the first range of wavelengths, of the fourth variation of the sixth aspect of the invention, corresponds to fluorescence emission radiation and the at least portion of the second range of wavelengths corresponds to phosphorescence emission radiation; (6) the additional steps of (f) receiving Raman emission radiation, directly or indirectly, from the sample at at least one second spectral filter which is capable of passing Raman emission radiation within a second range of wavelengths, which is different from the first range of wavelengths, along a second optical path; (g) measuring an amount of the Raman emission radiation within the second range of wavelengths using at least one second detector located directly or indirectly along the second optical path; (h) correlating information concerning the amount of Raman emission radiation within the second range of wavelengths measured by the at least one second detector with data associated with one or more chemical compounds of interest to provide at least partial chemical analysis of the sample; (7) the source being selected from the group consisting of: (a) a semiconductor source, (b) a an electron beam pumped semiconductor laser; (c) an electron beam pumped incoherent semiconductor source; and (d) an electron beam pumped AlGaN source; and (e) a hollow cathode laser; (8) the excitation radiation having a wavelength selected from the group consisting of (1) a wavelength less than 300 nm and (2) a wavelength less than about 250 nm; (9) at least one of the at least one first spectral filter or at least one second spectral filter, of the fourth variation of the sixth aspect of the invention, including a selected filter chosen from the group consisting of (a) a tunable filter; (b) a dispersive device; an acousto-optic tunable filter; a temperature tunable filter; (10) the chemical analysis is performed in conjunction with one or more sample handling or separation methods selected from the group consisting of: (1) capillary electrophoresis (CE), (2) capillary electrochromatography (CEC), (3) high performance liquid chromatography (HPLC), (4) microcapillary HPLC, (5) flow cytometry, (6) liquid flow cell methods, (7) air flow cell methods, and (8) a surface detection method; (11) a selected one of the at least one first spectral filter includes at least one angle tunable filter and the orientation of the at least one angle tunable filter, with respect to received emission radiation, is adjustable so as to enable the photoluminescence emission radiation that reaches the selected one of the at least one first detector to vary in wavelength; and (12) repeating the receiving and measuring operations, of the eleventh variation of the sixth aspect of the invention, with the at least one tunable filter tuned to different wavelengths so as to obtain data for a plurality of measurements for a plurality of wavelengths, wherein the correlating comprises determining relative amounts of the measurements for at least two different wavelengths of the plurality of wavelengths and comparing the relative amounts with the data. Further variations are also possible and include various mixtures of the above noted variations so long as such mixtures maintain the functionality of the method as a whole.

In a seventh aspect of the invention a chemical analysis apparatus includes: means for supplying a sample to be analyzed; means for applying excitation radiation from a semiconductor source having a wavelength less than about 300 nm directly or indirectly onto the sample; means for receiving emission radiation, directly or indirectly, from the sample at a spectral filter which is capable of passing a selected range of wavelengths of the emission radiation along a given optical path; means for measuring an amount of the selected emission radiation present using a detector located directly or indirectly along the selected optical path; means for correlating information concerning the amount of selected emission radiation measured by the detector with data associated with one or more chemical compounds of interest to provide at least a partial chemical analysis of the sample.

In an eighth aspect of the invention an apparatus for providing a chemical analysis of a sample includes: means for supplying a sample to be analyzed; means for applying radiation from an electron beam pumped semiconductor light emitting device directly or indirectly onto the sample; means for receiving emission radiation, directly or indirectly, from the sample at a spectral filter which is capable of passing a selected range of wavelengths of the emission radiation along a given optical path; means for measuring an amount of the selected emission radiation present, using a detector located directly or indirectly along the selected optical path; and means for correlating information concerning the amount of selected emission radiation measured by the detector with data associated with one or more chemical compounds of interest to provide at least a partial chemical analysis of the sample.

In a ninth aspect of the invention an apparatus for providing integrated chemical analysis of a sample includes: means for supplying a sample to be analyzed; means for applying excitation radiation directly or indirectly onto the sample; means for receiving emission radiation, directly or indirectly, from the sample at a $1^{st}$ spectral filter which is capable of passing a $1^{st}$ selected emission radiation along a $1^{st}$ optical path; means for receiving emission radiation, directly or indirectly, from the sample at a $2^{nd}$ spectral filter which is capable of passing a $2^{nd}$ selected emission radiation along a $2^{nd}$ optical path; means for measuring an amount of the $1^{st}$ selected emission radiation present using a $1^{st}$ detector located directly or indirectly along the $1^{st}$ optical path; means for correlating information concerning the amount of selected emission radiation measured by the $1^{st}$ detector with data associated with one or more chemical compounds of interest to provide at least a partial $1^{st}$ chemical analysis of the sample; means for measuring an amount of the $2^{nd}$ selected emission radiation using a $2^{nd}$ detector located directly or indirectly along the $2^{nd}$ optical path; and means for correlating information concerning the amount of $2^{nd}$ selected emission radiation measured by the $2^{nd}$ detector with data associated with one or more chemical compounds of interest to provide at least a partial $2^{nd}$ chemical analysis of the sample In a tenth aspect of the invention an apparatus for providing a chemical analysis of a sample, includes: means for supplying a sample to be analyzed, means for applying UV radiation directly or indirectly onto the sample; means for receiving radiation, directly or indirectly, from the sample at a tunable spectral filter which is capable of passing a selected radiation along a given optical path; detector means for measuring an amount of the selected radiation present which is located directly or indirectly along the selected optical path; and means for correlating information concerning the amount of radiation measured by the detector with data associated with one or more chemical compounds of interest to provide at least a partial chemical analysis of the sample.

In an eleventh aspect of the invention an apparatus for providing a chemical analysis of a sample, includes: (a) means for applying ultraviolet excitation radiation from a source directly or indirectly onto the sample to produce emission radiation in the form of Raman emission radiation within a first range of wavelengths and photoluminescence emission radiation within a second range of wavelengths; (b) first spectral filter means for receiving the emission radiation, directly or indirectly, from the sample and for passing the Raman emission radiation within at least a portion of the first range of wavelengths along a first optical path; (c) second spectral filter means for receiving the emission radiation, directly or indirectly, from the sample and for passing the photoluminescence emission radiation within at least a portion of the second range of wavelengths along a second optical path; (d) first measuring means for detecting an amount of the Raman emission radiation which is located directly or indirectly along the first optical path; (e) second measuring means for detecting an amount of the photoluminescence emission radiation located directly or indirectly along the second optical path; and (f) means for correlating information concerning the amounts of the Raman emission radiation and photoluminescence emission radiation measured by the first and second measuring means, respectively, with data associated with one or more chemical compounds of interest to provide at least a partial chemical analysis of the sample.

Variations of the eleventh aspect of the invention are possible and include functional counterparts and means plus function equivalents to those variations noted above for the fifth aspect of the invention In a twelfth aspect of the invention an apparatus for providing a chemical analysis of a sample, includes: (a) a source means for applying ultraviolet excitation radiation directly or indirectly onto the sample to produce emission radiation in the form of photoluminescence emission radiation within a first range of wavelengths; (b) a first spectral filter means for receiving the emission radiation, directly or indirectly, from the sample and for passing the photoluminescence emission radiation, within at least a portion of the first range of wavelengths, along a first optical path; (c) a first detector means for measuring an amount of the photoluminescence emission radiation located directly or indirectly along the first optical path; and (d) means for correlating information concerning the amounts of the photoluminescence emission radiation measured by the first means for detecting with data associated with one or more chemical compounds of interest to provide at least a partial chemical analysis of the sample.

Variations of the eleventh aspect of the invention are possible and include functional counterparts and means plus function equivalents to those variations noted above for the sixth aspect of the invention In a thirteenth aspect of the invention an apparatus for providing a chemical analysis of a sample includes: a window through which a sample to be analyzed can be irradiated; a semiconductor source capable of producing radiation having a wavelength less than about 300 nm and optically configured to direct radiation on to the window, a tunable filter located along an optical path which is capable of receiving emission radiation from a sample and for passing selected radiation, a sensor located on an optical path that extends from the tunable filter and is capable of providing an output indicative of the amount of selected radiation present; an electronic device capable of receiving input concerning the presence of selected radiation and to provide at least a partial chemical analysis of the sample.

In a fourteenth aspect of the invention an apparatus for providing a chemical analysis of a sample includes: an electron beam pumped semiconductor radiation emitting device; a spectral filter, a radiation sensor, an optical path extending from the radiation emitting device to a sample to be analyzed to the spectral filter and to the sensor, an electronic comparator electrically connected to the radiation sensor and to information about one or more chemical compounds of interest.

In a fifteenth aspect of the invention an apparatus for providing integrated chemical analysis of a sample includes: a source of narrow band radiation (e.g. ultraviolet radiation having a wavelength under 300 nm, more preferably under 280 nm, and even more preferably having a wavelength under 250 nm, and having a bandwidth less than 200 wavenumbers and more preferably less than 100 wavenumbers); a $1^{st}$ spectral filter; a $2^{nd}$ spectral filter; a $1^{st}$ radiation detector; a $2^{nd}$ radiation detector; a source of electronic data (e.g. an electronic storage device such as RAM, ROM, flash memory, a hard disk, internet connection, or the like) concerning one or more chemical compounds of interest, at least one electronic comparator (e.g. a computer programmed to compare stored data to measured data and potentially to derive conclusions based on the comparison); an initial optical path that directs, directly or indirectly, narrow band radiation from the source onto a sample to be analyzed; a $1^{st}$ optical path that directs, directly or indirectly, emission radiation from the sample to the $1^{st}$ spectral filter and then directs, directly or indirectly, $1^{st}$ selected radiation to the $1^{st}$ radiation detector; a $2^{nd}$ optical path that directs, directly or indirectly, emission radiation from the sample to the $2^{nd}$ spectral filter and then directs, directly or indirectly, the $2^{nd}$ selected radiation to the $2^{nd}$ radiation detector; a $1^{st}$ communication path that carries information from the $1^{st}$ detector to the at least one electronic comparator; a $2^{nd}$ communication path that carries information from the $2^{nd}$ detector to the at least one electronic comparator.

In a sixteenth aspect of the invention an apparatus for providing a chemical analysis of a sample includes: a UV laser; a tunable spectral filter for passing selected radiation; a radiation detector, an electronic data storage device, an electronic comparator for comparing stored data to measured data; an initial optical path that directs, directly or indirectly, radiation from the UV laser to a sample to be analyzed; a $1^{St}$ optical path that directs, directly or indirectly, emission radiation from the sample to the spectral filter and then directs, directly or indirectly, selected radiation to the radiation detector; a communication path that carries, directly or indirectly, information from the radiation detector to the electronic comparator.

In a seventeenth aspect of the invention an apparatus for providing a chemical analysis of a sample, includes: (a) a source of ultraviolet excitation radiation configured to direct the radiation on to a sample to be analyzed wherein the sample is capable of producing Raman emission radiation within a first range of wavelengths and photoluminescence emission radiation within a second range of wavelengths; (b) a first spectral filter configured to direct Raman emission radiation within at least a portion of the first range of wavelengths along a first optical path; (c) a second spectral filter configured to direct photoluminescence emission radiation within at least a portion of the second range of wavelengths along a second optical path; (d) a first detector located on the first optical path; (e) a second detector located on the second optical path; and (g) a computational device configured to correlate information concerning the amounts of the Raman emission radiation and photoluminescence emission radiation measured by the first and second detectors, respectively, with data associated with one or more chemical compounds of interest to provide at least a partial chemical analysis of the sample.

Variations of the eleventh aspect of the invention are possible and include functional counterparts and means plus function equivalents to those variations noted above for the fifth aspect of the invention In an eighteenth aspect of the invention an apparatus for providing a chemical analysis of a sample, includes: (a) a source of ultraviolet excitation radiation configured to direct the excitation radiation onto a sample to produce emission radiation in the form of photoluminescence emission radiation within a first range of wavelengths; (b a first spectral filter configured to receive the emission radiation and for passing the photoluminescence emission radiation, within at least a portion of the first range of wavelengths, along a first optical path; (c) a first detector located on the first optical path configured to receive and measure an amount of the photoluminescence emission radiation; and (e) a computational device configured to correlate information concerning the amounts of the photoluminescence emission radiation measured by the first detector with data associated with one or more chemical compounds of interest to provide at least a partial chemical analysis of the sample.

Variations of the eleventh aspect of the invention are possible and include functional counterparts and means plus function equivalents to those variations noted above for the sixth aspect of the invention Numerous additional variations of the first-eighteenth aspects of the invention are possible and include for example, mutatis mutandis, those variations specifically noted above for the fifth and sixth aspects of the inventions to the extent they apply to the other aspects without eliminating their functionality. For example, some variations of the first to third, seventh to tenth, and thirteenth to fifteenth aspects of the invention may include excitation radiation being applied from a source in the form of a semiconductor laser. In other variations, the excitation radiation may be supply from a incoherent semiconductor source.

Further aspects of the invention will be understood by those of skill in the art upon reviewing the teachings herein. These other aspects of the invention may provide various combinations of the aspects presented above as well as provide other configurations, structures, functional relationships, and processes that have not been specifically set forth above.

BRIEF DESCRIPTION OF THE DRAWINGS

FIG. 6A provides a simplified block diagram of components of a chemical analysis system according to a first class of analytical instrument embodiments of the invention.

FIG. 6B provides a block diagram illustrating examples of various types of analysis that the spectral filters can be tailored to provide.

FIG. 6C provides a block diagram illustrating examples of different types of spectral filters that may be used in conjunction with the first class of analytical instrument embodiments.

FIG. 6D provides a block diagram illustrating examples of different types of detectors that may be used in accordance with the first class of analytical instrument embodiments.

FIG. 6E provides a block diagram illustrating examples of different target forms in which the sample may be provided.

FIG. 6F provides a block diagram illustrating examples of environmental conditions under which sampling may be performed.

FIG. 7A provides a more detailed block diagram of components of a chemical analysis system according some embodiments in the first class of analytical instrument embodiments.

FIG. 7B provides a block diagram illustrating various examples of outputs associated with some chemical analysis systems of some of the embodiments of the first class of analytical instrument embodiments.

FIG. 8A provides a simplified block diagram of components of a chemical analysis system according to a second class of analytical instrument embodiments of the invention.

FIG. 8B provides a block diagram illustrating examples of different types of radiation sources that may be used in conjunction with the second class of analytical instrument embodiments.

FIG. 8C provides a block diagram illustrating examples of different types of tunable filters that may be used in conjunction with the second class of analytical instrument embodiments.

FIG. 10A provides a block diagram of a chemical analyzer package according to some embodiments of the invention where the package includes a power supply and a controller.

FIG. 10B provides a block diagram of a chemical analyzer package according to some embodiments of the invention where the package includes an output device while a power supply and/or analyzer may be separate from the package.

DETAILED DESCRIPTION OF PREFERRED EMBODIMENTS OF THE INVENTION

Deep UV Radiation Production Methods and Sources

To avoid the difficulties, set forth above, related to producing deep UV semiconductor sources, Applicants have developed a pumping approach that uses ballistic electron beam injection directly into the active region of a wide band gap semiconductor material. One element that distinguishes some embodiments of the invention from the teachings about electron beam pumping noted above is that none of the publications discuss, describe, or suggest the use of wide bandgap semiconductor materials (i.e. semiconductor materials having a band gap greater than 3.5 eV, corresponding to wavelengths less than 400 nm, more preferably greater than 4.15 eV, corresponding to wavelengths less than 300 nm, and most preferably greater than 4.97 eV, corresponding to wavelengths less than 250 nm). Furthermore these references fail to teach the use of Group III nitride semiconductor material systems, such as an AlGaN alloy, for producing laser output using ballistic electron beam pumping. These references also fail to teach the use of diamond for producing laser output using ballistic electron beam pumping. Another element that distinguishes some embodiments of the invention from these prior teachings is that they do not discuss, describe, or suggest producing lasers emitting below 300 nm, e.g. in the 200 nm to 300 nm range, using these wide bandgap semiconductor materials via ballistic electron beam pumping.

In contrast to a pn-junction laser device, where low energy electrons (e.g. electrons having an energy less than 5 to 10 eV) are used with each producing approximately one electron-hole pair, the ballistic electron injection approach uses high energy electrons (e.g. electrons having an energy on the order of 5 KeV to 10 KeV) are used with each electron entering the semiconductor material to successively lose its energy in multiple energy exchange collisions producing hundreds of electron-hole pairs. As a result, these electron-beam-pumped semiconductor ultra-violet optical source (ESUVOS) devices require about the same pumping power density as a pn-junction device, but at hundreds of times less current density and hundreds of times higher voltage. Employing the ESUVOS concept, miniature semiconductor incoherent and laser sources can be produced which emit in the wavelength range from about 200 nm to 365 nm simply by altering the alloy composition of the AlGaN material. In still other employments of the ESUVOS concept sources, e.g. laser or incoherent sources, emitting at about 227 nm may be produced using natural or synthetic diamond as the emission medium.

Figure 1:
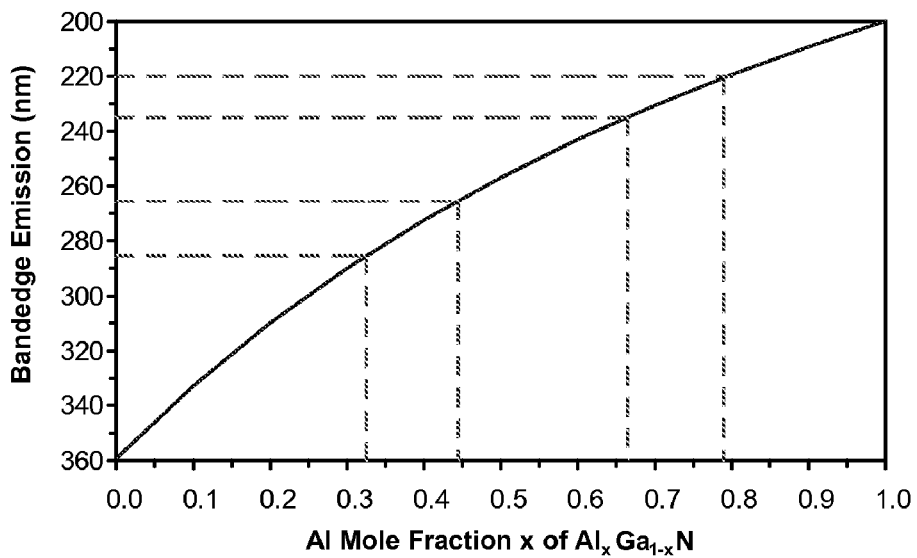
FIG. 1 provides a plot of band gap emission in nanometers versus mole fraction X of Al in $Al_x Ga_{1-x}N$.

The emission wavelength from aluminum-gallium-nitride (AlGaN) may be varied based on the aluminum mole fraction within the alloy, as shown in FIG. 1. Pure aluminum-nitride has a bandgap of 6.2 eV, corresponding to a 200 nm wavelength. Pure gallium-nitride has a bandgap of 3.6 eV, corresponding to a 360 nm wavelength. Intermediate bandgaps may be achieved by adding varying amounts (x) of aluminum in $Al_xGa_{1-x}N$. From FIG. 1 it can be seen that aluminum mole fractions greater than about 60% can achieve emission wavelengths below 250 nm.

As noted above, problems have presented themselves when trying to produce AlGaN semiconductor lasers having aluminum mole fractions greater than about 30%. The two primary problems include: (1) the inability to p-dope AlGaN alloys with the required Al content and (2) the inability to form ohmic contacts to AlGaN materials with high Al content. According to some embodiments of the invention, the problems with p-doping and ohmic contacts are addressed by directly pumping the bandgap using ballistic electrons from an electron gun (e.g. a field emission source). In some of these embodiments, the semiconductor material (e.g. AlGaN) and the electron source are contained in a highly evacuated or vacuum vessel (e.g. a miniature vessel). In other embodiments, one or both of the electron source and the semiconductor material may form portions of a hermetic envelope which allows a desired environment, e.g. an evacuated region, in which electrons may pass from the cathode to the semiconductor material. The vessel may also contain a source of acceleration voltage or one or more electrical feedthroughs that connect to such a source. The vessel may also contain a focusing and/or extraction grid (e.g. to focus electrons along a length of a gain medium that is to be excited).

The configurations of ESUVOS devices can take many forms and may be classed as incoherent light emitting devices or coherent light emitting devices (i.e. laser devices). In either class of device the semiconductor medium may include, for example, an aluminum gallium nitride alloy or range of alloys which are in the form of one or more epitaxially grown films located on a substrate material usually with a variety of buffer and cladding layers between the substrate and the optically active region of the film or films. The substrate material may, for example, be sapphire or silicon carbide, aluminum nitride, gallium nitride or other suitable materials compatible with the AlGaN epitaxial film or films. The optically active region of the film or films is preferably located at or close to the surface of the deposited materials, opposite the substrate, in order to minimize the scattering of ballistic electrons prior to generation of electron-hole pairs in the active region.

In the case of the incoherent light emitters, some of the devices may be termed electron-beam-pumped light emitting triode (ELET) devices as they typically have three electrodes (e.g. a cathode, an anode, and an extraction control grid). Other devices may have additional electrodes. As used herein triode shall generically be used to refer to radiation emitting devices that have an anode and a cathode and at least one intermediate electrode. In other words, unless further limited by the context, a triode device shall contain at least three electrodes but may contain more than three electrodes. In some embodiments of the invention a radiation emitting device may use only two electrodes (i.e. an anode and a cathode). If an extraction control grid is used, it may allow control of the electron current flowing between the cathode and anode. In ELET devices radiation emission is dominantly out the back surface of the substrate and may be enhanced by addition of a thin photon reflective film (e.g., 30 nm to 50 nm of aluminum on the surface of previously deposited films). In other words, the reflective film may be formed between the cathode and the semiconductor material and is made thin enough to allow electrons to pass through it to the semiconductor material while still providing optical reflectivity. This film (e.g. aluminum film) may serve as an anode as well as a mirror. As a mirror it may reflect the cathodoluminescent emission (produced from the active region of the semiconductor) in the original propagation direction of the electron beam, thereby increasing the radiance and power of the ELET source in that direction. The shape of the optical emission area is determined by the shape of the electron beam pumping current. In some embodiments, the electron beam may take on a circular geometry, which will produce a circular Lambertian emission profile, plus some edge emission from the ELET die. In other embodiments, the beam may take on an elongated configuration or some other configuration.

Such ELET devices may be constructed in different ways. For example, they may be constructed from processes similar to those used in the manufacture of semiconductor devices where individual functional and structural components are formed in situ in their desired configurations. In such processes it may be possible to form multiple devices, in whole or in part, on a single substrate or wafer after which dicing may occur to separate the individual devices (i.e. formation may occur in a batch process whereby multiple devices may be produced simultaneously on the same wafer or substrate). In other embodiments, a more traditional process may be used wherein some individual components of the devices may be formed separately and then placed in desired relative positions via an assembly process (e.g. the substrate, active semiconductor film, and anode may be produced in one process while the cathode and any control grids may be formed in one or more separate processes and then aligned and mounted in desired positions relative to the active semiconductor medium).

Figure 2:
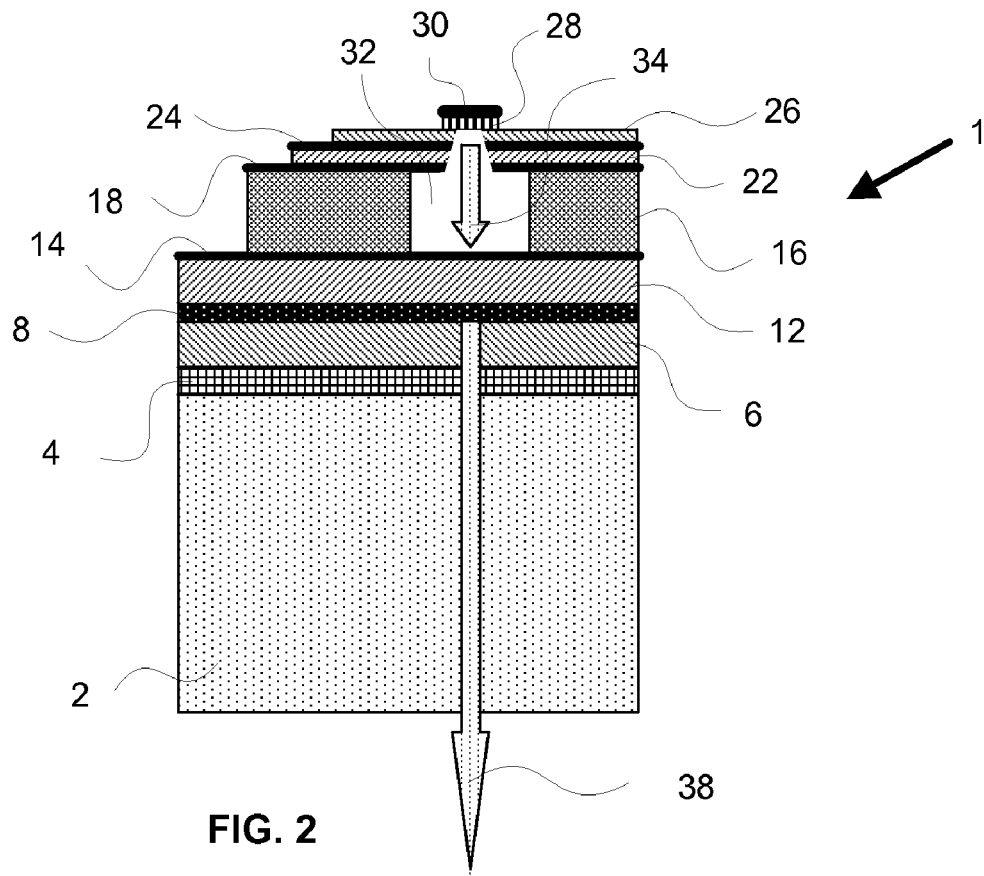
FIG. 2 provides a schematic cut view of an incoherent radiation producing electron-beam-pumped light emitting triode (ELET) device according to a first embodiment of the invention.

An example of an ELET device is illustrated with the aid of the cut view shown in FIG. 2. The device 1 of FIG. 2 includes a sapphire substrate 2, on which an aluminum nitride (AlN) buffer layer 4 is formed. In turn a graded cladding layer 6, e.g. of aluminum gallium nitride AlGaN, is formed. Immediately above the AlN layer, the gallium content of the cladding layer is low (e.g. starting at 0% to 30%) and increases to a concentration equal to or approaching that which an overlying active layer 8 of semiconductor material will have. The graded cladding layer may be formed from a plurality of separated applied layers having increasing Ga content.

The active semiconductor layer 8 is formed from one or more films of $Al_xGa_{1-x}N$ having mole fractional content "x" of Al and "1-x" of Ga which are intended to produce a desired wavelength or wavelength band of radiation.

The active layer is in turn overlaid by a graded cladding layer 12 formed of AlGaN which progressively decreasing gallium content. The graded cladding layer 12 is in turn overlaid by an anode contact layer (e.g. formed of aluminum which has a thickness appropriate to allow high energy electrons to pass through it and providing an optically reflective surface for photons generated in the active layer 8. As shown, the anode may have an exposed area (e.g. the upper left portion) which may be used to make electrical contact with a power supply via a wire bond or other conductive lead.

Overlaying the anode 14 is a patterned dielectric material 16. This dielectric helps define the electron acceleration gap between the anode and the cathode. It may be formed of any appropriate material and to have cross-sectional and height dimensions that allow appropriate excitation of semiconductor material to occur.

Overlaying the dielectric 16 is a focusing grid structure 18. It may include an exposed region for making electrical contact (e.g. the left most region of the layer). The focusing grid electrode 18 may be overlaid, in turn, by a patterned dielectric 22 which in turn may be overlaid by a patterned extraction gird layer 24. It may include an exposed region for making electrical contact (e.g. the left most region of the layer). The extraction grid layer may in turn be overlaid by a patterned dielectric 26 which in turn may support a cathode 28 (i.e. an electron source) which in turn may have an electrical contact 30 located on its upper surface. In some embodiments, the cathode may include a doped silicon substrate on which an array of carbon nanotubes are located. The Array may take any desired shaped which will result in an appropriate electron bombardment pattern onto the active material after the beam is focused by any focusing gird.

The layers 16-28 are patterned to form a void or gap 28 through which electrons can travel from the cathode to the anode when appropriate electrical power (i.e. current and voltage are applied to the cathode, anode, extraction grid and focusing grid. The gap may be surrounded by hermetic structures (not shown) which will allow a controlled environment to exist along the path taken by the shaped electron beam that is created. During operation radiation is produced within the active layer 8 and is emitted from the lower portion of the substrate, e.g. along path 38.

In some alternatives of this first example embodiment, the active layer may be deposited in a blanket fashion such that it exists over the entire prior deposit while in other alternatives it may be patterned deposited so that it exists in a region or regions that approximate the area or areas intended for excitation. Similar alternatives exist for the graded cladding layers and even the buffer layer. Similarly the anode layer may take the form a blanket or of a patterned deposit so that the anode exists in the regions to be excited, in a contact region and along a bridging path. In the case of patterned depositions regions not forming part of the active structure may be filled in with other materials. To minimize processing complexities and the risks of crystal structure mismatches and the like, the blanket formation alternatives are preferred.

In still other alternative embodiments, the AlGaN alloy and associated substrate, cladding layers, and buffer layers may be replaced by epitaxial deposited carbon (e.g. a diamond or diamond-like material) and appropriate substrate, cladding layers, and buffer layers. In still other alternative embodiments, the AlGaN alloy and associated substrate, cladding layers, and buffer layers may be replaced by a piece of a natural or synthetic diamond or diamond-like material that is appropriately shaped and which may or may not be attached to a substrate. Appropriate mirrors may be formed on one or more surfaces of the diamond, e.g. cleaved surfaces) or they may be located at a distance from diamond and held in place by appropriate mounting elements. The diamond or diamond-like material is preferably of high purity but it is possible that in some embodiments impurities may be included (via natural formation, doping, diffusion, or the like) and may result in minor or significant variations in diamond's nominal band-gap emission wavelength of approximately 227 nm.

In some alternative embodiments, the focus grid and/or the extraction grid may be removed. The various layers may each be formed as a single layer or as a plurality of layers. The anode contact may be located in a different location (e.g. below the upper cladding layer). The anode contact may not function as an effective mirror. The upper cladding layer may be removed or it may have a different height and/or concentration gradient and/or initial or final concentration levels that different from those used in the lower cladding layer. The beam may be made to leave a different surface of the structure. A second AlN buffer layer may be provided above the upper cladding layer 12 (e.g. below the anode layer 14).

In some embodiments, the ELET may be formed in part or entirely using semiconductor or MEMS (microelectromechanical system) fabrication techniques, while in other embodiments, it may be formed from a combination of semiconductor or MEMS fabrication techniques in combination with discrete component assembly operations, hermetic sealing and evacuating operations, and the like.

In various embodiments, the physical dimensions of various components may take on different values. In some embodiments, for example, the substrate may have a thickness in the range of 0.1 mm to 0.5 mm and have cross-sectional dimensions in the range of 0.2 mm to 1.0 mm In some embodiments the AlN layer above the substrate may have a thickness in the range of 100 nm to 2000 nm, the adjacent graded cladding layer may have thickness in the range of 10 nm to 100 nm, the active semiconductor regions may include multiple quantum wells (e.g. 10 to 50) with each including a layer of $Al_xGa_{1-x}N$ (e.g. having a thickness in the range of 0.1 nm to 1 nm separated by a layer of AlN (e.g. having a thickness in the range of 0.1 nm to 1 nm the graded cladding layer above the active semiconductor layer may have a thickness in the range of 10 nm to 70 nm, while an overlying AlN layer may have a thickness in the range of 100 nm to 500 nm, and an overlying anode or mirror layer may a thickness in the range of 10 nm to 100 nm. In some embodiments, the gap 32 may be in the range of 100-500 μm in height. In other embodiments, other dimensions may be used.

In some alternative embodiments one or more of the dielectrics 16, 24, and 28 that are located between the anode 14 and focusing grid 18, the focusing grid 18 and the extraction grid 24, and the extraction grid 24 and the cathode 28, respectively, may be replaced with other non-conductive structures and structural configurations that hold the electrodes in their desired relative positions (e.g. dielectric portions of a hermetic envelope in which the light source is located).

Laser versions of an electron-beam-pumped semiconductor ultra-violet optical source (ESUVOS) may take different forms. For example, they may take the form of (1) an edge emitter (i.e. radiation is emitted from a side or edge of the semiconductor film) or (2) a vertical cavity surface emitter (e.g. radiation is emitted the back surface of a semiconductor film into the substrate and then from the back surface of the substrate). In both forms, the device may take the form of an electron-beam-pumped laser triode, or ELT, similar to the ELET discussed above while in other forms more than three or less than three electrodes may be used. In either form, an electron beam may pump an optically active region near the surface of an epitaxial deposited layer of a semiconductor material such as, for example, an AlGaN alloy, diamond or diamond-like carbon, or it may pump a surface of a piece of natural or synthetically produced diamond or diamond-like carbon of desired shape.

In the case of the electron-beam-pumped vertical cavity surface emitting laser (EVCSEL) device, the electron beam pumps the semiconductor region in a fashion similar to that described above for ELET device except that mirror coatings are applied on both sides of the epitaxial film or piece of emission material or on surfaces parallel to the surfaces of the epitaxial semiconductor film or surfaces of the piece of emission material to form an optical resonant cavity for use at a desired design wavelength of the device (in some embodiments, thermal control may be used to obtain desired cavity length). In one simple case, the top and bottom of the AlGaN die are coated with a thin aluminum mirror coating (e.g. having a thickness of about 30 nm to 50 nm each) to form the resonant cavity. The thickness of the coating on the entry surface is limited on the one hand by a need to get the electrons into the active region and on the other by the need to form a mirror of desired reflectivity. The thickness of the coating on the back side (i.e. substrate side) of the active region is restricted only by the need to form a mirror of desired reflectivity. Alternatively, the mirror coatings may be applied on either side of the semiconductor material. For an EVCSEL, the electron beam current density needs to be higher than in the case of the ELET to enable the device gain to exceed device losses. In an EVCSEL the electron pumping beam may take on any desired cross-sectional shape, e.g. a circular shape. An example of an EVCSEL device is illustrated with the aid of FIG. 3.

Figure 3:
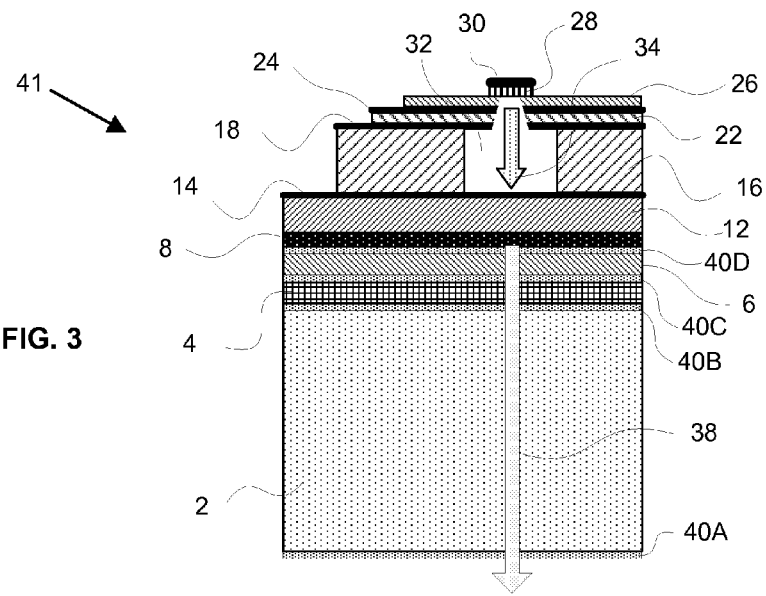
FIG. 3 provides a schematic cut view of an electron-beam-pumped vertical cavity surface emitting laser (EVCSEL) device according to a second embodiment of the invention.

The laser device 41 in the example of FIG. 3 is similar to the ELET device of FIG. 2 and, as such, similar elements are marked with similar reference numerals. The primary difference between the laser 41 of FIG. 3 and the incoherent source 1 of FIG. 2 is that the laser includes an additional mirror coating 40 that is applied to the substrate side of the active medium. As illustrated, in different embodiments, the mirror coating may be placed in different locations as indicated by references 40A, 40B, 40C, or 40D. The mirror coating will be located at one of the alternative locations 40A-40D as shown in the figure. In other alternative embodiments, the mirror may be located in still other positions, for example, it may be displaced from the lower surface of the substrate and held in position via appropriate alignment structures or standoffs. In embodiments where a piece of semiconductor, e.g. diamond, is used as the lasing medium, the cladding layers, buffer layers, and even substrate may be removed and the mirrors formed on or mounted to the surfaces of the semiconductor or they may be held by appropriate fixturing in a desired position relative to both the semiconductor material and the beam of excitation electrons used. In still other embodiments, additional optical components may be added, such as Brewster windows, direction reorienting mirrors, prisms or the like. The mirror may or may not be located within an evacuated chamber created to allow free electrons to travel to the anode/semiconductor material with minimal energy losses. The mirror positioning shown with reference 40A is preferred for many embodiments as the mirror coating material (e.g. aluminum, will not interface with any desired crystal matching between the material junctions in the epitaxially deposited films.

In the case of an edge emitting electron-beam-pumped laser (EEEL) device, the electron beam typically takes a planar form so that it essentially forms a line of incident electrons on the semiconductor material which is to be activated. The line may be formed from a single elongated emission zone or a plurality of discrete but closely spaced emission regions. The long dimension of the incident beam extends along an axis of the active semiconductor medium. The activated medium emits radiation in all directions (including out of the upper and lower surfaces of the gain medium and out of the edges of the medium). A pair of mirrors are used to define an optical gain path that extends through and to opposite edges of the activated medium. In some embodiments, the mirrors may be located on and bonded to cleaved facets of the semiconductor medium while in other embodiments, the mirrors may be spaced from the semiconductor material. In this case, the ballistic electron beam produces a gain region along the optical axis defined by the mirrors.

Figure 4A:
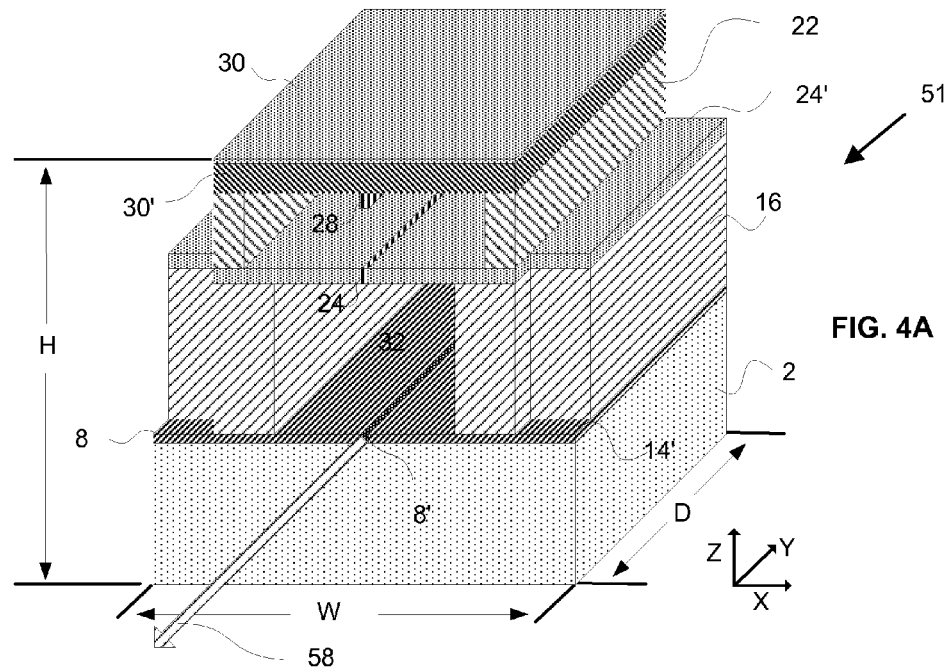
FIG. 4A provides a perspective view of an electron-beam-pumped edge emitting laser (EEEL) device according to a third embodiment of the invention.

A first example of an EEEL device is shown in the perspective view of FIG. 4A. Portions of the device that are similar to those in FIGS. 2 and 3 are indicated with like reference numerals.

In this embodiment the laser 51 includes a sapphire substrate 2 which may have a width dimension, W, in the range of 250-750 μm (e.g. 500 μm) and a depth dimension, D, in the range of 350-1050 μm (e.g. 700 μm). The overall height, H, of the laser may, for example, be in the range of 300-1200 microns (e.g. 500 μm. The laser produces a beam 58 from an edge of the excited AlGaN semiconductor material 8. Mirrors or reflective surfaces (not shown) are located on the front and back faces of the semiconductor. These mirrors form a resonant cavity. These mirror surfaces may be limited to height and/or width regions corresponding to the region of the semiconductor material that is to be excited and from which desired radiation is to be emitted. In other embodiments, the entire front and back surfaces of the substrate, semiconductor, and additional layers may be coated. In still other alternative embodiments, the mirror coatings may be displaced from the semiconductor material and held in place by appropriate surfaces and spacers or alignment fixtures. The mirrors may be formed within a hermetic envelope, form part of a hermetic envelope, or be located outside a hermetic envelope. In some alternative embodiments, additional optical elements may be located between the semiconductor material and the mirrors.

The semiconductor material, e.g. AlGaN of having appropriate fractional mole concentration of Al, may be formed on various layers of other materials (not shown) which are deposited on the substrate material and it may also be over-coated with additional layers of various materials. For example, buffer layers, cladding layers, and/or an anode material through which electrons can pass to excite the semiconductor material and to which electrons can be drawn after excitation.

As shown, an electric contact 14' for the anode may be formed on a portion of the semiconductor material or on one of the overlying layers. Preferably the portion of the semiconductor material 8', located between the cavity mirrors, is excited so as to maximize the gain of the system. The X&Y dimensions of the semiconductor material excited by an electron beam traveling in the Z direction may be controlled by controlling either the X & Y dimension of the semiconductor material and/or by controlling the X & Y dimensions of the bombarding electron beam. The absorption of the electrons along the Z-dimension may be tailored to occur within the semiconductor material by selecting the bombardment voltage (e.g. to maximize laser output) and/or by selecting the thickness of the semiconductor material and/or the thicknesses of and materials chosen to overlay the semiconductor material.

Above material 8, a gap 32 exists in which a vacuum is preferably created. This vacuum may be limited to this gap region, it may surround all or a portion of the semiconductor material and/or its substrate, and/or the cathode (to be discussed herein after). In the various embodiments, the vacuum region may be defined by a hermetic envelope. The hermetic envelope may surround all or a portion laser components shown in FIG. 4A. In some embodiments, a portion of the laser components shown in FIG. 4A may form parts of the hermetic envelope. In some embodiments, a getter material may be located within the hermetic envelope to help maintain the integrity of the vacuum. In some embodiments the gap 32 may be, for example 100-500 µm in height. In this gap, electrons are accelerated toward the anode to cause hole/electron creation in the active semiconductor material. Above the gap a cathode 28, such as a linear carbon nanotube (CNT) array, is located which is supported by a cathode substrate 60, for example a doped silicon substrate). The CNT array 28 has a length that corresponds to the length of an excitation path in the active semiconductor material 8 along which laser radiation will be produced. In some alternative embodiments, instead of using a linear array of carbon nanotubes, a diamond microtip field emission array may be used, or even a thermionic emission cathode may be used.

In gap 32, between and separated from the CNT Array and the anode, an optional extraction grid 24 is shown s which includes an elongated opening or array of openings (each, for example, having a 2 µm diameter) through which electrons can pass. The cathode and extraction grid are configured to give rise to a slit shaped electron beam which impinges on the active semiconductor material 8 to produce an excited medium which can give rise to laser radiation from the edge of the semiconductor device. The device also includes cathode contact 30, and a grid contact 24' and appropriate distances between the anode, the cathode, and the extraction grid may be set and maintained by dielectric materials 16 and 22.

Upon application of appropriate voltages and current, a laser beam 58 may be generated. This laser beam 58 may, for example, be used to irradiate a sample or surface of a sample to be analyzed. In some embodiments, for example, the field emission elements may be set at zero volts, the extraction grid may set at minus 10 volts while the anode may be set at plus 5000 volts. In other embodiments an electron lens structure may be provided between the extraction grid and the anode to help focus the electron beam onto the active semiconductor target (e.g. AlGaN target).

Figure 4B:
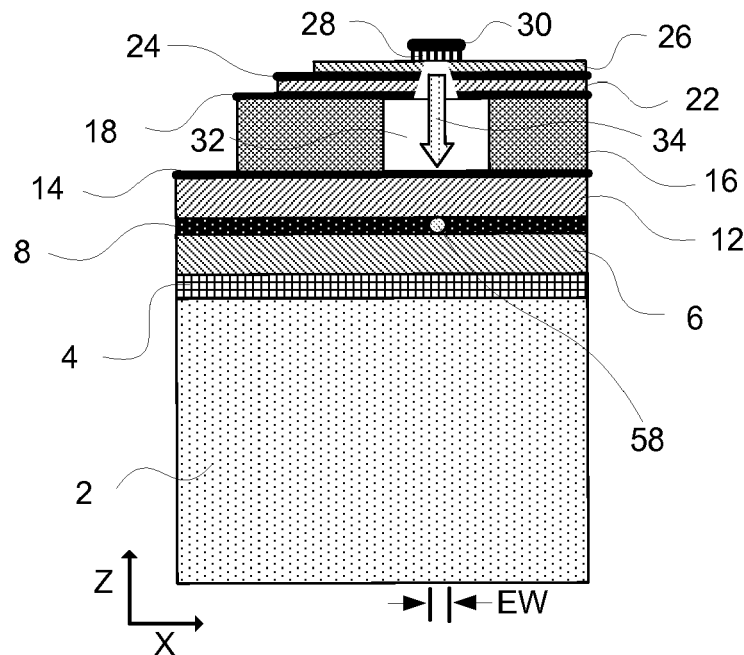
FIGS. 4B and 4C provide schematic cut views of an electron-beam-pumped edge emitting laser (EEEL) device according to a fourth embodiment of the invention where the cuts are taken along two perpendicular axes.
Figure 4C:
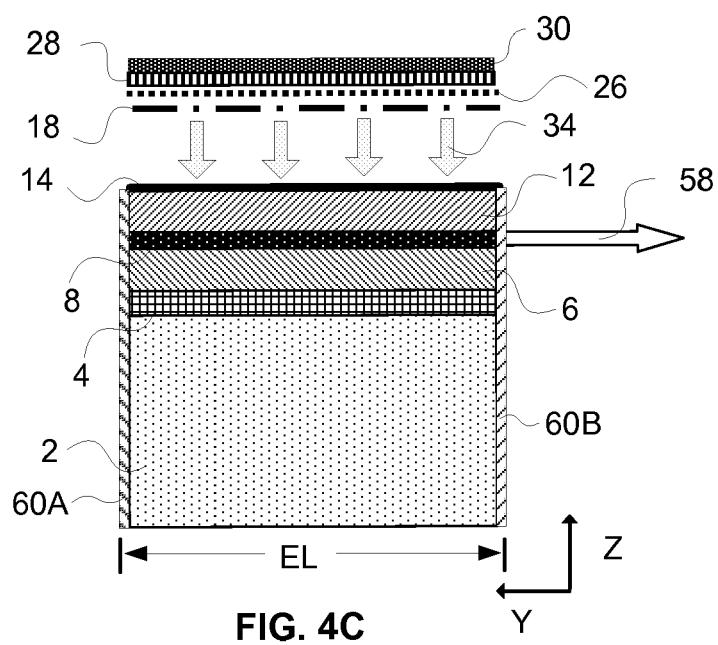

FIGS. 4B and 4C provide cut views of an example EEEL device. Like elements of FIGS. 4B and 4C are depicts with similar reference numerals to those used in FIGS. 2-4A. The device is similar but not identical to that of FIG. 4A. FIG. 4B depicts a cut view in the X-Z plane while FIG. 4C depicts a cut view in the Y-Z plane. In FIG. 4C the laser beam 58 can be seen projecting from the left side of the device while FIG. 4B shows the laser beam having a circular cross-section and being projected out of the plane of the figure. FIG. 4B depicts dielectric standoffs 16, 22, and 26 which cannot be seen in FIG. 4C. FIG. 4C depicts the electron beam has having a length EL while FIG. 4B depicts the electron beam as having a width EW. FIGS. 4B and 4C depict several deposited layers which are located on substrate 2. These layers include (1) a buffer layer 4, e.g. formed of AlN, (2) a graded cladding layer 6, e.g. formed of AlGaN and having an increasing Ga content with height, (3) the active semiconductor layer or layers 8, e.g. formed of AlGaN having a mole fraction of Al selected to produce radiation of a desired output wavelength, (4) a graded cladding layer 12, e.g. formed of AlGaN with an Al concentration that decreases with height, and (5) an anode layer 14, e.g. formed of aluminum through which excitation electrons may pass. In some alternative elements a buffer layer may be including between cladding layer 12 and anode layer 14. In still other embodiments, fewer deposited layers may exist while in other more deposited layers may exist. In still other embodiments, the types of materials deposited may be different or a substrate of different material may be used. In FIG. 4C, cavity mirrors 60A and 60B may be seen. In some embodiments, mirror 60A may be highly reflective while mirror 60B may be partially reflective (e.g. with reflectivity chosen to yield desired gain and desired output. In other embodiments, other reflectivity configurations may be used, e.g. both mirrors may be partially reflective so that a beam is emitted from both ends of the device.

In various embodiments of the invention, whether devices are of the ELET type, the EVCSEL type, or of the EEEL type, the various layers of deposited materials may have various thicknesses. For example, an AlN layer above the substrate may have a thickness in some embodiments in the range of 100 nm to 1500 nm (e.g. about 1000 nm), an adjacent graded cladding layer may have thickness in the range of 10 nm to 100 nm (e.g. about 70 nm), an active semiconductor regions may include multiple quantum wells (e.g. between 20-100, e.g., about 50) with each including a layer of $Al_xGa_{1-x}N$ (e.g. having a thickness in the range of 0.1 nm to 1.5 nm, e.g. 1 nm) separated by a layer of AlN (e.g. having a thickness in the range of 0.1 nm to 1.0 nm, e.g. 0.3 nm), a graded cladding layer above the active semiconductor layer may have a thickness in the range of 10 nm to 100 nm, (e.g. about 70 nm), while an overlying AlN layer may have a thickness in the range of 100 nm to 1000 nm, e.g. about 500 nm.

As noted in the above examples, it is typical for ESUVOS devices of the present invention to make use of an extraction grid or gate sealed in a hermetic volume through which the electrons flow and which may extend beyond or be bounded by the cathode on one end and the surface of the semiconductor gain medium on the other. However, it should be understood that other configurations are possible. ESUVOS devices may not involve use of an extraction grid or gate but use other means to control the electron beam current. Such other means may include current limited power supplies, feedback loops keyed off radiation production or detected current flow, or the like.

Sources of electrons can be, for example, simple thermionic sources or more advanced field emission devices such as, for example, carbon nanostructures (e.g. nanotubes), diamond microtip arrays, or similar naturally negative electron affinity devices with electric field enhancement in the form of, for example, very sharp pointed electron emitter arrays. These electron sources have demonstrated the ability to emit the required, approximately 10 to 100 A/cm$^2$, current densities needed to adequately pump AlGaN laser devices. The required pumping current density is several orders of magnitude lower than that typically used in pn-junction laser devices. However, the electron energy is also several orders of magnitude higher, so that the pumping power density remains about the same.

Photon emission media other than AlGaN (i.e. gain medium in the case of a lasing device) may be used. For example, pure or substantially pure diamond, of the natural or synthetic type, may be pumped by a high energy electron beam such that band gap photon emission at about 227 nm is excited. The diamond may be epitaxially deposited on buffer and cladding layers on a substrate or instead may take the form of an appropriated shaped piece of naturally occurring or synthetically produced diamond or diamond-like carbon. The medium may be appropriately shaped, e.g. cleaved or sliced, from a natural source or it may be cleaved or sliced from a boule of synthetically produced diamond. The diamond piece may take on a variety of shapes. For example, it may be substantially pill shaped in the case of an ELET or EVCSEL device or it may be elongated, or rod-like, in the case of an EEEL device.

Figure 5A:
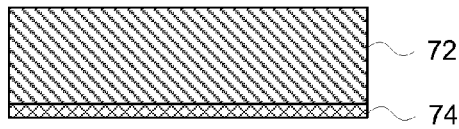
FIGS. 5A-5F provide schematic depictions of various states in a process of forming a semiconductor laser according to some embodiments of the invention.
Figure 5B:
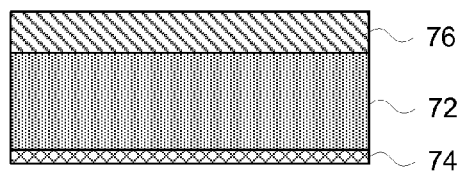
Figure 5C:
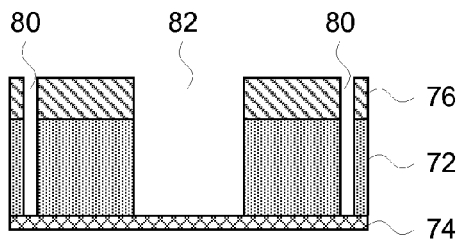
Figure 5D:
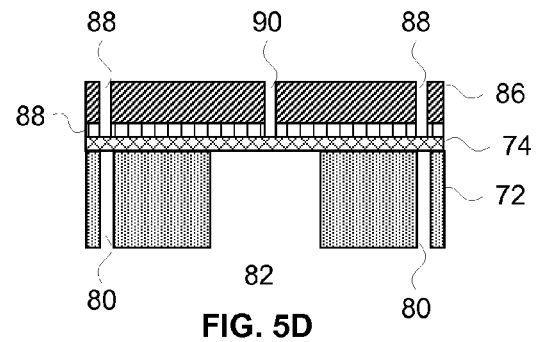
Figure 5E:
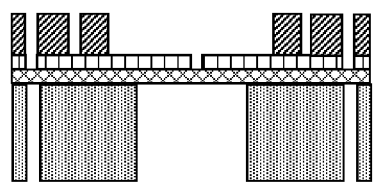
Figure 5F:
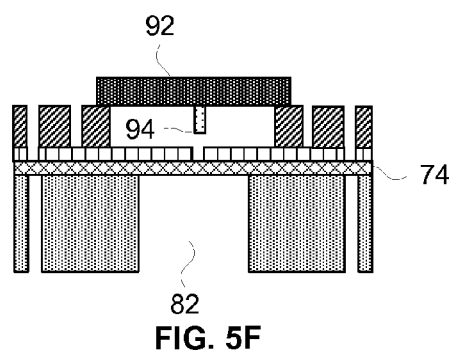

FIGS. 5A-5F provide schematic depictions of various states in an example process of forming the grid and cathode portion of a semiconductor laser according to some embodiments of the invention. FIG. 5A depicts a silicon wafer 72 having a thickness of, for example, about 300 µm, and whose lower surface has received a layer of silicon oxide, SiO, 74. FIG. 5B depicts the state of the process after the top side of the silicon wafer has received a coating of thick photoresist (PR)) 76. FIG. 5C depicts the state of the process after the photoresist 76 has been patterned and the silicon wafer 72 etched through (e.g. using DRIE etching) to form dicing lanes 80 and large gird aperture 82 and leaving intact the layer of silicon oxide 74. FIG. 5D depicts the state of the process after (1) the structure of FIG. 5C is inverted, (2) the photoresist 76 has been removed, (3) a combined coating 84 of chromium (Cr) followed by gold (Au) has been applied (e.g. by sputtering), (4) a coating of photoresist 186 has been applied to the gold and patterned to form openings 90 corresponding to locations where grid openings/apertures (elongated array of openings) will be located and openings 88 corresponding to dicing lines, and (5) the chromium and gold layers have been etched away in the areas 190 and 188 via the openings in the photoresist. FIG. 5E depicts the state of the process after the photoresist is further patterned and developed to create grid contacts and leaving photoresist on top of grid. FIG. 5F depicts the state of the process after (1) the SiO 74 is dissolved in the region of opening 82 to create a chip with a suspended grid, (2) a cathode support 92 and cathode 94 (e.g. including a carbon nanotube array) is bonded (e.g. glued) to photoresist to yield a cathode located above the openings in the grid array.

Other steps or operations (not shown) may be performed. For example grid wires may be added. The grid and cathode portion may be bonded, directly or indirectly to a piece of semiconductor photon emission material (e.g. diamond or diamond-like carbon) that may or may not be attached to a substrate. The grid and cathode portion may be bonded to an emission medium formed from deposited layers (e.g. including a buffer layer, graded cladding layers, an active semiconductor material, and an anode material) on a substrate (e.g. a sapphire substrate). In other embodiments, the grid and cathode portion may not be bonded to the semiconductor material but each may be mounted in relative positions via appropriate fixed or adjustable mounts. In some embodiments, the formation of the cathode, gird and support structure may be formed on a device-by-device basis while in other embodiments, batch formation may be used. Similarly, device-by-device formation may be employed in attaching the sapphire substrate and active semiconductor material to the cathode/grid assembly or batch processing and then dicing may be used. Similarly mirror coating may be applied on a device by device basis or via batch processing.

In some alternative embodiments the grid and cathode portion of a device formed according to the process of FIGS. 5A-5F may be implemented on a working substrate comprising a piece of the semiconductor emission material, with or without a primary substrate, or on the epitaxially grown layers of material located on a primary substrate.

Various alternative formation processes may be used, various other alternative design configurations are also possible, and/or various changes may be made to the materials used in the formation of various portions of the radiation source (i.e. laser or incoherent source). These variations and changes will be apparent to those of skill in the art upon review of the teachings herein.

Analytical Methods and Instruments

Various embodiments of the invention provide novel analytical methods and/or instruments for providing at least partial chemical analysis of samples. FIG. 6A provides a simplified block diagram of components of a chemical analysis system or apparatus according to a first class of analytical methods and instrument embodiments of the invention. The system 100 includes a semiconductor laser 102 (e.g. a laser of selected from one of the types discussed above) which produces radiation 104 which is used to illuminate a sample 106 (which is typically not part of the apparatus). In preferred embodiments of the invention, the radiation 104 impinging on the sample is in the ultraviolet (i.e. UV) range. The apparatus may include a window through which the sample may be irradiated and through which resulting radiation may be received; a cavity in which the sample may be placed, the sample irradiated, and resulting radiation produced; a transparent tube in which a quantity of the sample may be flowed, irradiated, and resulting radiation detected; or the like (not shown). Different types (or bands) and wavelengths of radiation 108 may come from sample 106 as a result of irradiation by the semiconductor laser. Depending on the excitation radiation 104, the wavelengths 108 coming from sample 106 may be, for example, of the Rayleigh type, Raman type, fluorescence type, or phosphorescence type. The resulting radiation 108 may be in the ultraviolet range (i.e. UV), visible range, or even IR range.

The radiation 108 coming from sample 106 is made to impinge directly (i.e. without intermediate optics, e.g. mirrors, lens, filters, diffraction gratings, or the like) or indirectly (i.e. via at least one optical component) on at least one spectral filter 112 which in turn passes (e.g. transmits or reflects) selected radiation 114, if present in incident radiation 108, onto one or more radiation detectors 116. The radiation detector may then produce a signal 118 (e.g. an electrical signal) that is sent to an analyzer 122 (e.g. a programmable electronic device) that compares information coming from the detector(s), along with information corresponding to the wavelengths passed by filter 112, to data stored about one or more known elements, molecules, or the like. The analyzer produces a result which may be indicative of a recognized relevant substance, indicative of a recognized but irrelevant substance, indicative of an inconclusive or unrecognized substance, indicative of a need to perform additional analysis, and/or indicative of a relative concentration or quantity of the substance present, or the like).

In some variations of the first class of embodiments set forth in the block diagram of FIG. 6A the semiconductor laser may be of the EEEL type while in other variations it may be of the EVCSEL type. In other alternative embodiments, the semiconductor laser may be replaced by an incoherent source such as an LED or ELET (e.g. embodiments where fluorescence and/or phosphorescence detection will be performed).

In some alternative embodiments the analyzer may be replaced by an output device that transmits information about the detected radiation to a separate device which performs the analysis function.

In some other alternative embodiments, the system may also include a receiver (e.g. a hardwired, IR, or microwave communication link) for obtaining instructions and or comparison data from an external device.

In some alternative embodiments the device may include a control panel for receiving input from an operator. It may also include one or more of a visual display, an audio signaling subsystem, and/or a tactile (e.g. vibrational) subsystem for communicating selected information to an operator or to persons located in the vicinity of the device. In some alternative embodiments, the system may include output signal capability that can be used to control external devices such as fans, doors, sprinklers, and the like. These functionalities may be provided for example via one or more appropriately programmed microprocessors, appropriately configured state machines, associated temporary and permanent memory, and associated input and output subsystems which are within the skill of the art.

According to some embodiments of the invention, preferred deep ultraviolet light sources, and most particularly laser sources, are small (e.g. under a volume of 4 liters, more preferably under a volume of 2 liters, even more preferably under a volume of 0.5 liters, and most preferably under a volume of 0.125 liters), light weight (e.g. light enough to be held in the hand, more preferably weighing less than 20 pounds, even more preferably weighing less than 5 pounds, and most preferably weighing less than 2 pounds), and consume only small amounts of power (e.g. consuming under 100 watts average power during operation, more preferably under 10 watts, even more preferably under 2 watts, and most preferably capable of being powered from one or more batteries). Such ultraviolet sources may enable many analytical instrument applications which may benefit from the use of induced native fluorescence or Raman spectroscopy to detect and identify unknown chemical substances. Semiconductor lasers, of the type discussed above, can enable such applications. According to some embodiments of the invention, such semiconductor lasers can be fabricated which emit in the ultraviolet range (i.e. wavelengths below 400 nm), and preferably at wavelengths below about 300 nm, and even more preferably at wavelengths below about 250 nm.

Figure 11A:
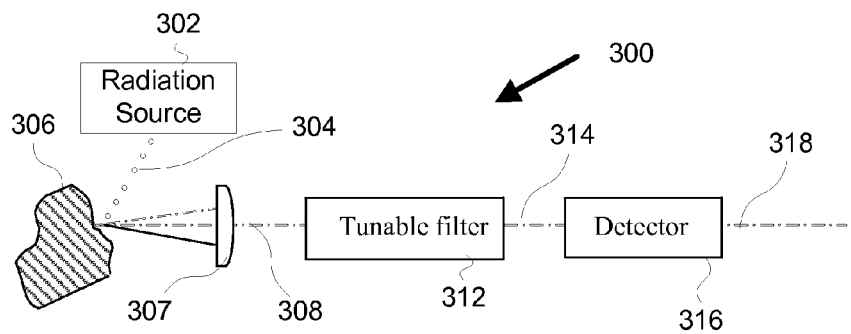
FIG. 11A provides a schematic illustration of a chemical analysis system according to some embodiments of the first class of embodiments.

Some embodiments of the invention provide analytical methods and/or instruments for providing at least partial chemical analysis of samples. FIG. 11A provides a simplified schematic diagram of components of a chemical analysis apparatus or system according to a first class of analytical instrument embodiments of the invention. The system 300 includes a semiconductor laser 302 that produces ultraviolet (UV) radiation 304 (e.g. radiation having a wavelength less than about 300 nm) that is used to bombard or expose a sample 306 (this sample is not typically considered part of the apparatus or device). Preferred wavelengths of radiation are below 300 nm, more preferably below 280 nm, even more preferably below 250 nm but in other embodiments it may be possible to use longer wavelengths of radiation or even shorter wavelengths of radiation.

The apparatus may include (1) a window, e.g. formed of quartz or other UV transmitting material, through which the sample may be irradiated and through which resulting radiation may be received; (2) a cavity in which the sample may be placed, the sample irradiated, and resulting radiation produced; (3) a transparent tube in which a quantity of the sample may be flowed, irradiated, and resulting radiation detected; or the like (not shown). Different types (or bands) and wavelengths of radiation 308 may come from sample 306 as a result of irradiation by the semiconductor laser 302. Depending on the excitation radiation 304, the wavelengths 308 coming from sample 306 may be, for example, of the Rayleigh type, Raman type, fluorescence, or phosphorescence type. In still other embodiments where higher energy incident photons 304 are used, Rayleigh scattering may be detected and used to analyze properties in a very thin layer at the surface of a sample. The resulting radiation 308 may be in the ultraviolet range (i.e. UV), visible range, or even IR range.

The radiation 308 coming from sample 306 is made to impinge directly (i.e. without intermediate optics, e.g. mirrors, lens, filters, diffraction gratings, or the like) or indirectly (i.e. via at least one optical component) 307 on at least one spectral filter 312 which in turn passes (e.g. transmits or reflects) selected radiation 314, if present in the incident radiation 308, onto one or more radiation detectors 316. The radiation detector may then produce a signal 318 (e.g. an electrical signal) that is sent to an analyzer, e.g. a programmable electronic device, (not shown) that compares information coming from the detector(s), along with information corresponding to the wavelengths passed by filter 312, to data stored about one or more known elements, molecules, or the like. The analyzer produces a result which may be indicative of a recognized relevant substance, indicative of a recognized but irrelevant substance, indicative of an inconclusive or unrecognized substance, indicative of a need to perform additional analysis, and/or indicative of a relative concentration or quantity of the substance present, or the like. In various alternative embodiments, the analyzer may perform additional functions or simply perform different functions depending on the needs dictated or desired in various potential circumstances. The analyzer may be a single device or multiple devices.

In other embodiments, instead of producing photons that undergo filtering and then detection, an optical beam induced current, surface electrovoltage spectroscopy, or the like may be used to provide analytical characterization of a sample.

In some variations of the first class of chemical analysis embodiments set forth in the block diagram of FIG. 6A the semiconductor laser may be or may include an electron beam pumped semiconductor laser.

In some alternative embodiments the analyzer may be replaced by an output device that transmits information about the detected radiation to a separate device which performs the analysis function.

In some other alternative embodiments, the system may also include a receiver (e.g. a hardwired, IR, or microwave communication link) for obtaining instructions and or comparison data from an external device.

In some alternative embodiments the device may include a control panel for receiving input from an operator. It may also include one or more of (1) a visual display, (2) an audio signaling subsystem, and/or (3) a tactile (e.g. vibrational) subsystem for communicating selected information to an operator or to persons located in the vicinity of the device. In some alternative embodiments, the system may include output signal capability that can be used to control external devices such as fans, doors, sprinklers, or the like. These functionalities may be provided for example via one or more appropriately programmed microprocessors, appropriately configured state machines, associated temporary and permanent memory, and associated input and output subsystems which are within the skill of the art.

FIG. 6B provides a block diagram illustrating examples of various types of analysis that may be performed by various embodiments of the first class of embodiments. The type of analysis performed is determined by the relationship between the radiation incident on a sample and the type of radiation coming from the sample and as such for a given incident wavelength, the type of analysis performed is related to the spectral filters chosen. As indicated, the chosen spectral filters 112 may result, for example, in a Raman analysis 204, a fluorescence analysis 206, a phosphorescence analysis 207, a combined or two-step or even three step analysis 208-211. Two step analyses may include fluorescence and Raman 208, phosphorescence and Raman 209, or fluorescence and phosphorescence 210. In some two-step embodiments the measurements of each type of analysis, for example, may be performed simultaneously, one or both measurements may be performed at one or more predetermined times after extinction of incident radiation bombardment onto the sample that is being analyzed, one or both analysis may include more than one measurement which may be performed at one or more offset times so that resultant radiation output decay over time may be determined and used in performing the analysis. In some embodiments, the each of the two analyses may be performed independently and conclusions drawn and then compared to determine, confirm, or fine tune the analyses. In other embodiments, one analysis may be performed and preliminary conclusions drawn and then the other analysis may be performed in a manner which is based at least in part of the results of the first analysis. In some embodiments, three step analysis (i.e. Raman, fluorescence, and phosphorescence 211) may be performed with similar variations as noted for the two-step analysis as well as additional variations due to the presence of further degrees of freedom associated with the existence of the third step or analysis type.

Both phosphorescence intensity and phosphorescence decay rate are useful parameters in the identification of unknown materials. When one or both are combined with measurement of Rayleigh, Raman, and/or native fluorescence emissions, a wide range of information is made available for the description of the unknown chemical and materials under investigation.

FIG. 6C depicts examples of various types of spectral filters 112 that may be used in various embodiments according to the first class of embodiments. In particular the spectral filters may be divided into two primary classes (1) tunable filters 214 and (2) dispersive filters 224. Tunable filters are filters that pass a given wavelength or wavelength band depending on how they are tuned while dispersive filters pass a number of wavelengths or wavelength bands simultaneously where energy associated with different wavelengths is found at different angles relative to an incident beam that is directed onto the filter. Three examples of tunable filters are set forth in FIG. 6C, angle tunable filters 215, acousto-optic tunable filters 218, and temperature tunable filters 220. Two examples of functionality are provided for angle tunable filters and temperature tunable filters: (1) monochromator functionality 216 and 221, respectively, and fixed functionality 217 and 222, respectively. The monochromator functionality results in the examination of a plurality of wavelengths in a serial manner while fixed functionality is provided by the filter being used in single radiation passing configuration. For the acousto-optic filter, a single, monochromator 219, functionality is exemplified. The dispersive filters, on the other hand, in combination with appropriate detector elements or arrays, may provide spectrographic functionality 227 by collecting a complete spectrum simultaneously, scanning monochromator functionality 225 or fixed monochromator functionality 226.

Raman instruments can be divided into two basic types: (1) spectrometers and (2) monochromators. Spectrometers collect complete spectra simultaneously (using a dispersive filter element) while monochromators collect only one wavelength at a time. Monochromators may, e.g., use photomultiplier tubes or avalanche photodiodes as radiation detectors but only to measure one wavelength or waveband at a time. Multi-channel charge coupled devices (CCD's) may be used in spectrometers to detect multiple wavelengths simultaneously.

Looked at in a different way, monochromators can be divided into two types: dispersive and non-dispersive. Dispersive monochromators employ a dispersive device such as a prism or grating. Although the resolution of a dispersive monochromator depends solely on the number of grooves in the grating and the order of the spectrum, in practical terms the resolution depends on the focal length of the instrument. The longer focal length instruments have higher spectral dispersion and higher resolution. Non-dispersive monochromators may use any of a variety of tunable filters including Fabry-Perot filters, thin-film dichroic interference filters, liquid crystal tunable filters, acousto-optic tunable filters, and temperature tunable filters. Tunable filters have the advantage that they are typically wide-area devices that enable high efficiency radiation collection when used as single point detectors.

A major disadvantage of tunable filters is that they allow transmission of only one Raman waveband at a time. Therefore, in order to measure spectra (e.g. Raman spectra) it is necessary to adjust the filter one wavelength-band at a time to collect a complete Raman spectrum. Multi-channel detectors in conjunction with dispersive filters have come into wide use in Raman spectroscopy because of a "multi-channel advantage". This advantage is due to the Raman scattered photons being collected simultaneously at all Raman shifts, thereby collecting all scarce Raman scattered photons resulting from a given level and duration of excitation. This advantage is especially valuable when the number of Raman spectral resolution elements, $N_R$, is large. The signal-to-noise ratio of multi-spectral-channel spectrometers is $N_R^{1/2}$ times greater for multi-channel instruments than for single-channel instruments.

However, if an instrument is a dedicated quantitative analyzer that monitors only a few Raman lines, for example, and a complete spectrum is unnecessary, tunable filters provide several advantages. First, since they require no dispersion, their resolution is not limited by the size of the instrument. Raman analyzers using tunable filters can be made very compact. Second, since their resolution is not restricted by entrance slit or array detector element dimensions, tunable filters have much larger area and higher etendue (geometrical extent), and are therefore more efficient than spectrographs or dispersive monochromators. This fact alone may make up for any losses due to the multi-channel advantage if the number of lines of interest is less than about 10. In some embodiments, beam splitting may be used to direct radiation from the sample to an array of filters each having a single-channel detector (i.e. each detector is positioned to measure a specific shift). Such beam splitting techniques allow the signal-tonoise advantages of multi-channel detection without the need for collecting contiguous spectral elements as is done in a multi-channel spectrograph.

Thin film dielectric filters may be used in some embodiments as angle tunable filter 215. The Military Standardization Handbook, MIL-HDBK-141, published on 5 Oct. 1962 describes in detail the history, theory and practice of making multi-layer interference filters of a wide variety of types including narrow band, wide band, long pass, short pass, as well as other filter types over a wavelength range from the ultraviolet to the infrared. For bandpass filters the center wavelength can be adjusted by adjusting the filter angle, which is the angle between filter axis and the optical axis. This is also discussed in the book, "Thin-Film Optical Filters" by Angus Macleod, which was most recently republished in 1989. Both of these references are incorporated herein by reference. In some embodiments ultra-narrow band filters are used having a full width at half maximum less than about ten Angstroms, more preferably less than five angstroms, and even more preferably less than about two angstroms.

When the filter angle is increased the center wavelength shifts toward the blue. The amount of wavelength shift is typically 10 nm to 15 nm over an angular rotation of 30 degrees. As the filter is rotated, the filter bandpass becomes wider and can typically double as a result of an angle change of 30 degrees. Filter wavelength change as a function of angle was fully described in Section 20 of MIL-HDBK-141. Wavelength, $\lambda$(nm), can be converted to wavenumber, $v$(cm$^{-1}$), since the wavenumber is the reciprocal of wavelength:

$$v(\text{cm}^{-1})=10^7/\lambda(\text{nm}).$$

With regard to Raman analysis, the difference between the excitation frequency of the laser and the center frequency of the filter is the Raman shift position of the filter, $v_R$. This is given by:

$$v_R = 10^7\{1/\lambda_L - 1/\lambda_0[1-(N_a/N^*)^2 \sin^2\theta]^{1/2}\}$$

where $v_R$ is the Raman shift position of the filter in wavenumbers (cm$^{-1}$), $\lambda_L$ is the wavelength of the excitation radiation in nm, $\lambda_0$ is the center wavelength of the filter at normal incidence to the optical axis in nm, $N_a$ is the ambient index of refraction of air, $N^*$ is the effective index of refraction of the filter materials and $\theta$ is the angle between the filter axis and optical axis.

Angle tunable infrared bandpass filters have been employed in Raman spectroscopic instruments since the mid-1990s. Batchelder, et.al. employed an infrared bandpass filter with a bandpass of a few nanometers. The 785 nm wavelength laser used for excitation in this instrument had an angle tuning range about 500 wavenumbers. Because of this limited range, a series of filters were employed, as described in U.S. Pat. No. 5,194,912, to cover a reasonable range of Raman shift. The teachings of this patent are incorporated herein by reference. Unfortunately, bandwidth at these wavelengths typically doubles between a filter angle of zero and about 22 degrees. At 45 degrees the filter bandpass is nearly triple the value at perpendicular incidence. Because of this, angle tunable filters have typically not been used much beyond an angle of 30 degrees, or so.

In the deep ultraviolet where the many advantages of Raman signal enhancement occur and background fluorescence is eliminated, the range of Raman shift which can be covered by angle tuning a filter is approximately 4 times greater than in the infrared at 785 nm, going to about 2000 wavenumbers in the UV compared to only 500 wavenumbers in the IR. This allows fewer UV filters to be used to cover a desired wavenumber range.

Temperature tuning of the center wavelength of bandpass filter is another alternative to angle tuning. Typical filters have a temperature coefficient measured in nanometers per degree Centigrade ranging from about 0.015 at 250 nm to about 0.020 at 800 nm. Munroe, et.al. demonstrated in 1997 that a 244 nm filter could be tuned as much as 500 wavenumbers by heating the filter to 100° C. The tuning range in the infrared is much less, being only about 22 wavenumbers at an excitation wavelength of 785 nm.

Acousto-optic tunable filters (AOTF) are especially attractive devices for wavelength selection in Raman analyzer instruments operated in the ultraviolet. The following equation illustrates that the bandwidth of the filter decreases as the square of the wavelength such that at 250 nm, the resolution of a 2 cm long AOTF is less than 10 wavenumbers. Added advantages of this type of tunable filter are that it is rapidly tunable from Raman band to Raman band, has no moving parts, and can be gated in synchronism with pulsed ultraviolet lasers to reduce the power consumption and heating of the device and to provide higher signal-to-noise measurements of Raman emissions.

$$\Delta\lambda = 0.9\lambda_0^2/\Delta nL \sin^2\theta_i$$

where $\Delta\lambda$ is the full width at half maximum of the bandwidth of the AOTF, $\lambda_0$ is the laser excitation wavelength, $\Delta n$ is a constant property of the AOTF, L is the interaction length of the AOTF crystal, and $\theta_i$ is the polarization angle of the incident Raman scattered radiation.

AOTFs are especially valuable when used in conjunction with pulsed lasers which have low operating duty cycles. Quartz is primarily used as the AOTF media because of its transparency in the ultraviolet. Because the acousto-optic coefficient of quartz is low, quartz AOTFs typically require a large amount of drive power and therefore require water cooling. However, when a quartz AOTF is operated at low duty cycles as would be desired when matched to low duty cycle pulsed lasers, the average power consumption becomes sufficiently low that water cooling is not necessary. Taking advantage of this fact can lead to reduced size, reduced weight, and lower complexity analytical analysis system.

In ultraviolet based embodiments, by adjusting the temperature of a filter or angle of the filter with respect to an optical axis of incident radiation, the center wavelength position of the filter band-pass can be changed over a wide range of Raman wave bands (e.g. shifts up to several thousand wavenumbers may be obtained using a single filter). This is in distinct contrast to longer wavelength systems that require a plurality of filters to cover a desired Raman band of wavelengths. This helps enable very simple and compact UV Raman point or area sensors of wide utility.

In some, non-ultra-violet embodiments, a chemical imaging system which employs a liquid crystal tunable filter (LCTF) as the spectral tuning element may be used. LCTFs do not function at deep visible or ultraviolet wavelengths and are therefore not useable for imaging in the ultraviolet.

FIG. 6D provides a block diagram illustrating examples of different types of detectors that may be used in accordance with the first class of embodiments. A wide variety of detectors are available for use with tunable filters 112. Point detection is used when measurements are intended to be made at one point on a sample. Single channel detectors include simple photodiodes 256, avalanche photodiodes 244, or photomultipliers 236. If two-dimensional imaging of the emission of a single line is desired, various two dimensional array detectors may be used, such as for example photomultiplier arrays 238, photodiode arrays 258, CCD arrays 264, image intensified CCD (ICCD) arrays 266, electron-beam CCD (EBCCD) arrays, or electron-multiplying (EMCCD) 268. Each of these detectors is available in ultraviolet sensitive models for which high quantum efficiencies are available.

FIG. 6E provides a block diagram illustrating examples of different target forms in which the sample may be provided.

FIG. 6F provides a block diagram illustrating examples of environmental conditions under which sampling may be performed.

FIG. 7A provides a more detailed block diagram of components of a chemical analysis system according some embodiments in the first class of analytical instrument embodiments. The block diagram of FIG. 7A shares various components and functional relationships with those of FIG. 6A. Elements 102, 106, 112, and 116 are common to both block diagrams and so are functional relationships (in terms of radiation flow between components) 104, 108, and 114. In addition to these common elements and relationships, the embodiments corresponding to the block diagram of FIG. 7B may include (1) optional optical elements located along the optical path between the laser 102 and the sample 106, (2) optional optical elements located along the optical path between the sample 106 and the spectral filter(s) 112, (3) optional optical elements located along the optical path between the filter(s) 112 and the detector(s) 116, (4) a power supply or source of power (e.g. a battery) 126, (5) an optional controller 128, and (6) an analyzer 122 and an output device 124, at least one of which is optional.

The controller 128 may include one or more input devices or components such as a keyboard, a mouse, a control panel, or the like. The controller may control operation of various components of the system and it may include a programmable electronic device such as a microprocessor and a memory. The controller and the analyzer may be part of the same component. For example, the controller may control the powering on and off of the radiation source and/or it may control a shutter or tuning element to provide well controlled timing of sample irradiation and correlated or timed measurements for all or selected portion of the re-emitted radiation (e.g. timed measurements for fluorescent and phosphorescent emission). If the optional analyzer is included in the system, a separate output device may not be necessary. If the optional output device is included in the apparatus, the optional analyzer may be separate from the apparatus. The optional optical elements may include mirrors, lenses, filters, splitters, apertures, and the like which may be useful for performing a variety of functions, for example: (1) folding optical paths to reduce the size of the apparatus, (2) focusing radiation onto selected components, (3) removing undesired radiation, (4) splitting beams into multiple components, and the like.

FIG. 7B provides a block diagram illustrating various examples of outputs associated with some chemical analysis systems of some of the embodiments of the first class of embodiments.

In some alternatives to the embodiments of FIGS. 7A and 7B, the electron beam pumped semiconductor laser may be replaced with an incoherent source, such as an LED or and ELET device.

FIG. 8A provides a simplified block diagram of components of a chemical analysis system 400 according to a second class of embodiments of the invention. The chemical analysis system 400 includes elements similar to those found in the block diagram of FIG. 6A with the exception that the semiconductor laser is replaced by a UV laser that may be a semiconductor laser or a different type of laser (e.g. a hollow cathode laser) or even a non-coherent radiation emitting device such as an ELET device, and the generic spectral filter(s) of FIG. 6A are replaced by one or more tunable spectral filters 214.

FIG. 8B provides a block diagram illustrating examples of different types of radiation sources that may be used in conjunction with the second class of embodiments. Examples of semiconductor lasers and incoherent sources have been more fully discussed herein before and examples of hollow cathode lasers are discussed in detail in U.S. Pat. No. 6,693,944, entitled "Sputtering Metal Ion Laser" and issued to Hug et al. This referenced patent is incorporated herein by reference as if set forth in full herein.

FIG. 8C provides a block diagram illustrating examples of different types of tunable filters that may be used in conjunction with the second class of embodiments. This figure is similar to the tunable filter portion of FIG. 6C and the reader is directed back to that discussion for more information concerning examples of alternative filter types that may be used.

Figure 11B:
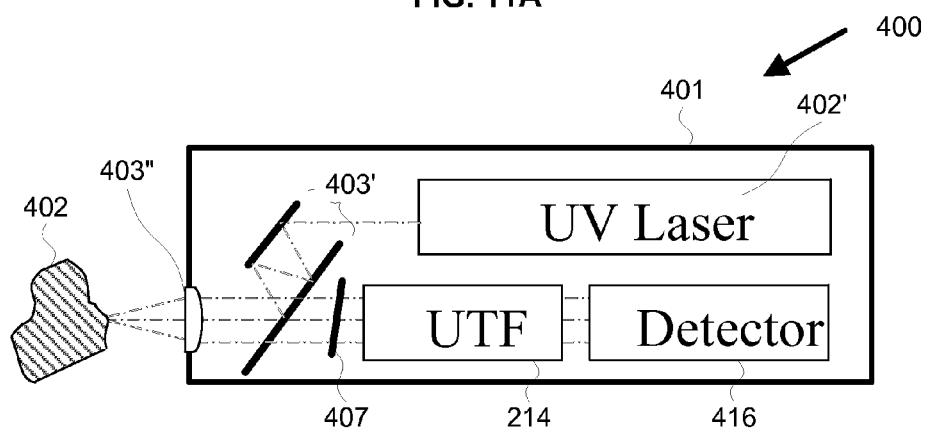
FIG. 11B provides a schematic illustration of a chemical analysis system according to some embodiments according to the second class of embodiments.

FIG. 11B provides a schematic illustration of a chemical analysis system 400 according to some embodiments of the second class of embodiments. The system includes a package 401 which holds a UV laser radiation source 402, a UV tunable filter 214 and a detector 416. The package 401 additionally holds a multi-bounce filter 403', a lens 403", and a Rayleigh edge filter 407. Radiation from source 402 is directed onto filter 403' which folds the optical path and directs the radiation through lens 403" onto sample 402. Radiation coming from sample 402 is passed back through lens 403", passes through one element of the multi-bounce filter 403' onto Rayleigh edge filter 407 which removes the Rayleigh radiation and passes any detectable radiation of interest to the tunable filter 214. The tunable filter 214 passes selected radiation onto detector 416 based on how it is tuned. Signals corresponding to detected radiation can be carried to an output device and/or an analyzer (which are not shown but which may be located within the package 401 or external to it and which may be part of the system). An analyzer may compare information about one or more wavelengths of measured radiation to a library of information about known substances to determine what substance or substances are present or alternatively to determine if a particular substance or substances are present. The analyzer may take the form of a programmable electronic device (e.g. a microprocessor and memory) which may also function as a controller for the laser, the tunable filter, and the detector. In some variations of this embodiment, the package may also include an electrical power source in the form of a battery, capacitor, photocell or the like.

Figure 9A:
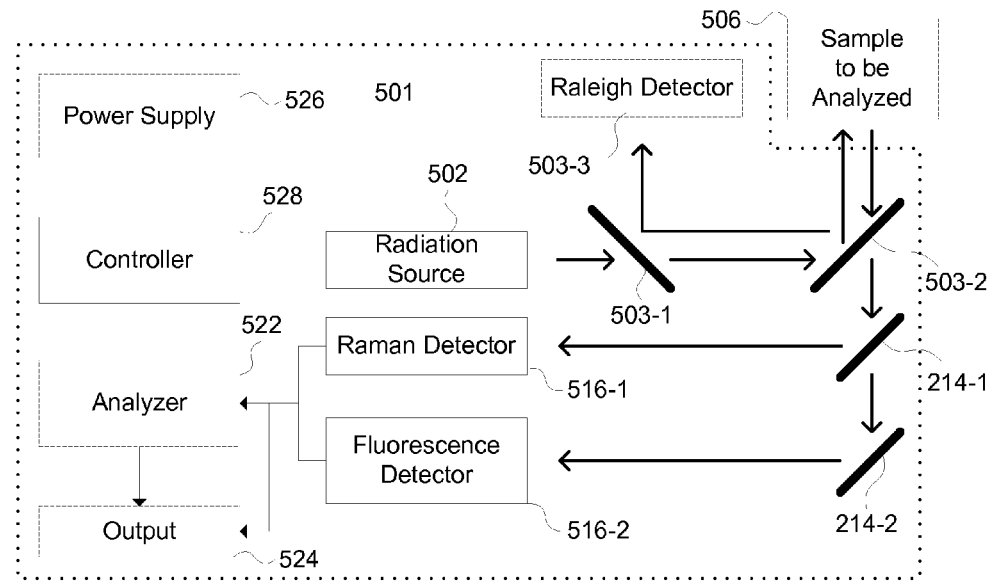
FIG. 9A provides a block diagram of components of a chemical analysis system according to a third class of analytical instrument embodiments of the invention.

FIG. 9A provides a block diagram of components of a chemical analysis system according to a third class of analytical instrument embodiments of the invention. In the class of embodiments of FIG. 9A, multiple spectral filters are provided along with multiple detectors. Embodiments of this class may simultaneously measure different types of spectral information (e.g. Raman and fluorescence as illustrated)) or alternatively, the system may be controlled to only measure one type of spectral information (e.g. fluorescence or Raman) until a substance of possible interest is identified and thereafter a second type of analysis (e.g. Raman or fluorescence) may be performed to obtain further information about the substance or to further distinguish the substance. In some variations of the embodiments of this class, prior to performing secondary analysis (e.g. Raman analysis) a sample may be concentrated (e.g. positive detections from a one or a plurality of successive primary analyses may be used to cause (e.g. via blowing, sucking, or electrostatic attraction) such samples (e.g. air born or liquid born particles) to move into a trap so as to increase concentration for subsequent analysis by the secondary analysis technique.

The system of FIG. 9A provides a package 501 in which a radiation source 502 is located along with a Raman detector 516-1 and a fluorescence detector 516-2 and at least two spectral filters 214-1 and 214-2 for respectively directing $1^{St}$ and $2^{nd}$ selected radiations on to detectors 516-1 and 516-2. The package may also include filter 503-1 and filter or mirror 503-2, Rayleigh detector 503-3, power supply 526, controller 528, and analyzer 522 and/or output device 524. The package may also include a stepper motor, linear motor, or other electronic or electromechanical devices for tuning any tunable filters that are present.

In the chemical analysis method involving the device of FIG. 9A, radiation is directed from the radiation source 502 to sample 506. Return radiation is directed onto filter 503-2 where Rayleigh radiation is reflected toward filter or mirror 503-1 of which a portion may be directed to Rayleigh detector 503-3. Radiation of detection interest is passed by filter 503-2 and encounters filter 214-1 which reflects $1^{St}$ selected radiation to the Raman detector 516-1 and transmits other radiation of detection interest onto filter 214-2. Filter 214-2 reflects $2^{nd}$ selected radiation onto fluorescence detector 516-2 and may transmit or absorb other wavelengths that are not of interest. In some alternative embodiments, if only $2^{nd}$ selected radiation is transmitted by filter 214-1 the second filter 214-2 may not be necessary. Signals from detectors 516-1 and 516-2 are sent to Analyzer 522 directly or via an output device 524, e.g. in those embodiments where the analyzer does not form part of the instrument. Based on the results produced by analyzer 522, the controller 528 may implement different method options (e.g. programmed routines).

In some alternative embodiments, the fluorescence detection of the example of FIG. 9A may be replaced with phosphorescence detection so that a combination of phosphorescence and Raman detection is provided. In still other embodiments, the Raman detection may be replaced with phosphorescence detection such that combined phosphorescence and fluorescence analysis is provided. In case of either phosphorescence or fluorescence, the measurements may be made during irradiation of the sample or at one or more times after irradiation. The timing of irradiation and measurement, as well as analysis, may be performed by the controller and/or may be controlled by an external device that communicates with the controller. In embodiments where phosphorescence or fluorescence is measured after irradiation is stopped, it may be possible to eliminate one or more of the filters shown in FIG. 9A.

When fluorescence is measured, it may be desirable to make one or more measurements in the range of 0.1 nS to 100 nS after extinguishing the application of excitation radiation to the sample so as to cover decay times that may be typical for the substances of interest. When phosphorescence is measured, it may be desirable to make a plurality of measurements over a period in the range of 0.5 mS to 0.5 S after extinguishing the application of excitation radiation so as to cover decay times that may be typical for the substances of interest. In some embodiments, the fluorescence detection and phosphorescence detection may use a common detector, or set of detectors, and a common spectral filter, or set of filters. Of course in some embodiments repeated measurements of fluorescence or phosphorescence may occur over longer ranges or shorter ranges of time and may even occur during sample irradiation. In some embodiments, it may be useful in helping to distinguish fluorescence emission from phosphorescence emission by not only measuring appropriate spectral amounts during emission decay (i.e. after extinguishing excitation radiation) but also to make one or more timed measurements after initially applying excitation radiation to the sample so as to determine emission build up profiles as well.

In some embodiments, the spectral filters 214-1 and 214-2 may scan through a plurality of different wavelengths so that different wavelength ranges are allowed to reach their respective detectors at different times. As another example, in some other embodiments one or more additional spectral filters may be located between the primary filters 214-1 and 214-2 and their respective detectors to provide a desired level of wavelength specificity. As a further example, in still other embodiments additional spectral selectively may be built into the detector components themselves.

Figure 9B:
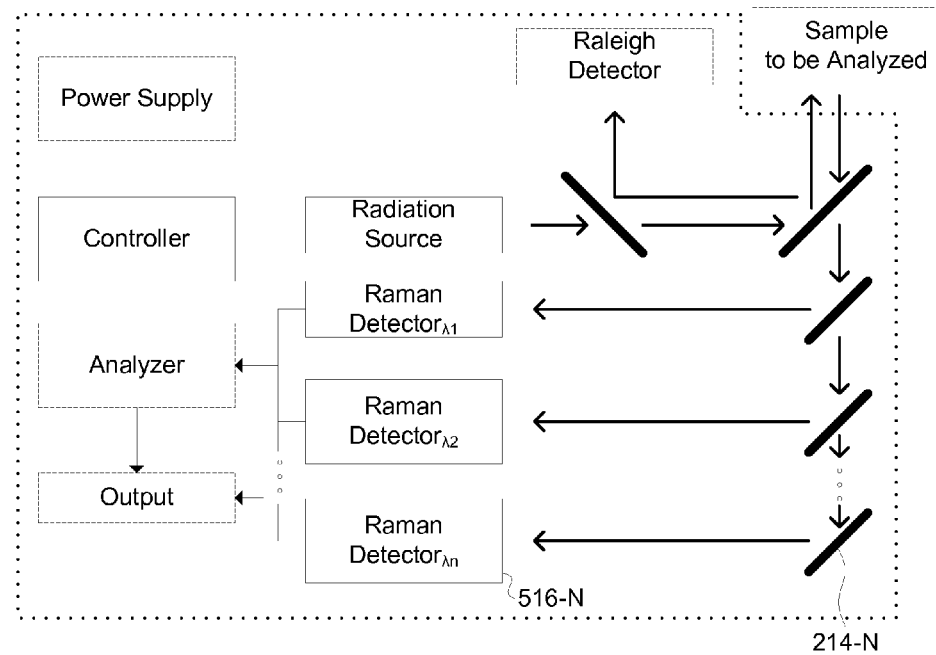
FIG. 9B provides a block diagram of components of a chemical analysis system according to a fourth class of analytical instrument embodiments of the invention.

FIG. 9B provides a block diagram of components of a chemical analysis system according to a fourth class of analytical instrument embodiments of the invention. The system of FIG. 9B allows multiple Raman wavelengths ($\lambda_1, \lambda_2, \ldots, \lambda_N$) of interest to be simultaneously detected. The components of FIG. 9B are similar to those of FIG. 9A with the exception that extra spectral filters up to 214-N and detectors up to 516-N are included and where each of the filters 214-1 to 214-N are tailored to pass to detectors 516-1 to 516-N selected bands of Raman wavelengths of interest. In some alternative embodiments, the multiple Raman detectors and spectral filters may be replaced or supplemented by fluorescence and/or phosphorescence detectors and filters to provide multiple simultaneously detected bands of Raman, fluorescence and/or phosphorescence data.

Figure 9C:
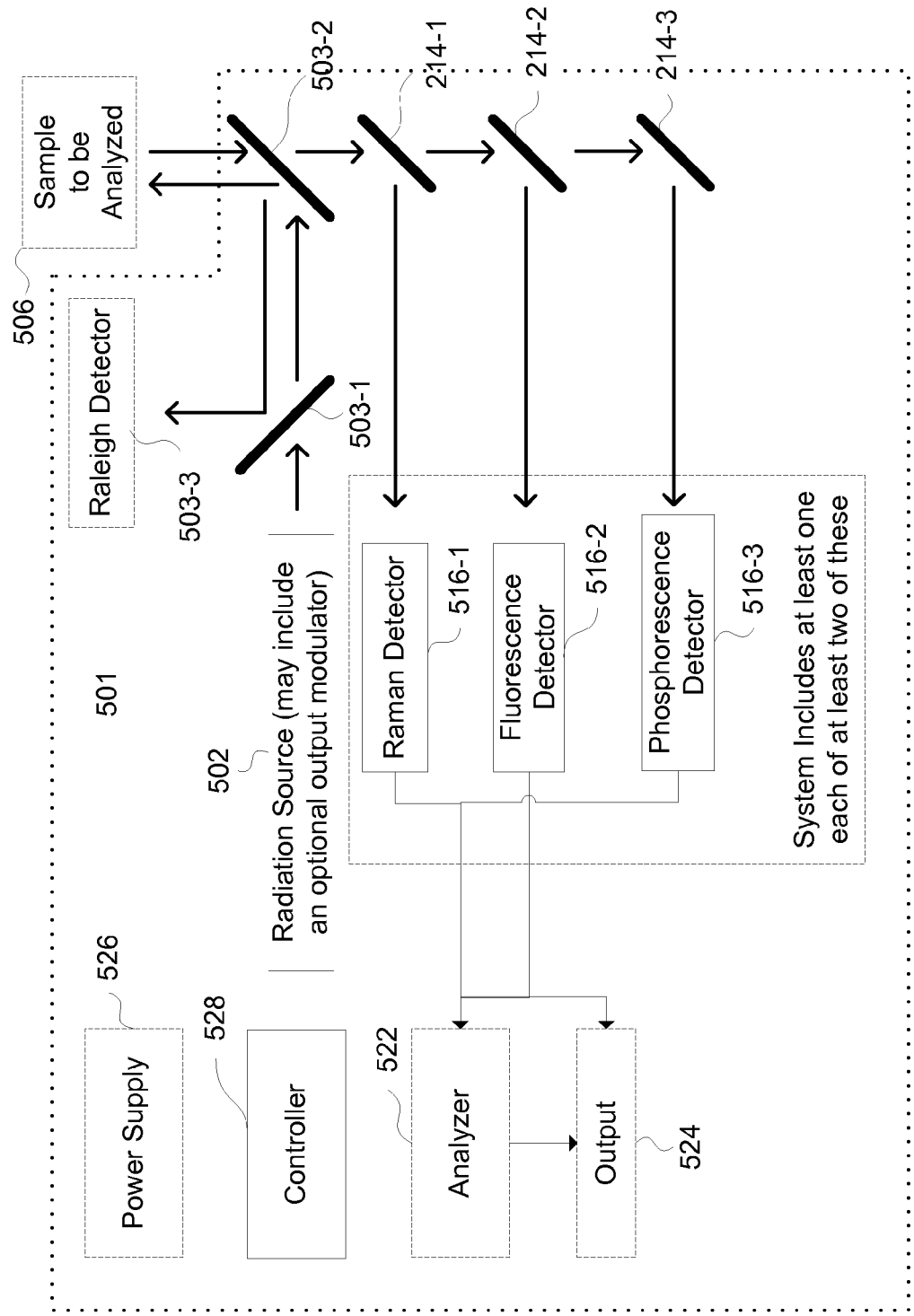
FIG. 9C provides a block diagram of components of a chemical analysis system according to a fifth class of analytical instrument embodiments of the invention.

FIG. 9C provides a block diagram of components of a chemical analysis system according to a fifth class of analytical instrument embodiments of the invention. The system of FIG. 9C has many elements in common with that of FIG. 9A and as such these elements are marked with the same reference numerals as those of FIG. 9A. The embodiment of FIG. 9C adds phosphorescence as an additional detection system or analysis method compared to that of FIG. 9A. In this embodiment, the fluorescence filter 214-2 and detector 516-2 and phosphorescence filter 214-3 and detector 516-3 are shown as being separate though in other embodiments they may be shared since fluorescence and phosphorescence emission bands typically largely overlap and thus could also use the same spectral filters and detectors particularly since these two types of emission are typically differentiated by decay times that differ by one or more orders of magnitude. Fluorescence decay times are typically in the 100 pS to 10 nS range and phosphorescence decay times are in the 0.5 mS to 100 mS range. These decay rates may allow useful measurements to be made for these emission types during different time periods, e.g. during a time range of 100 pS to 100 nS for fluorescence and during a range of 0.5 mS to 1000 mS for phosphorescence (as measured from the extinction of the excitation radiation). The use of separate fluorescence and phosphorescence detectors or at least additional phosphorescence detectors, as shown in FIG. 9C, may be warranted since phosphorescence often extends to longer wavelengths than fluorescence.

The radiation source 502 in FIG. 9C is also explicitly shown as optionally including an output modulator (e.g. an acousto-optic modulator) that may be used to precisely control excitation radiation regardless of laser radiation build up or decay time. In other embodiments there may not be a need for such an independent modulator. For example, in some embodiments, the laser or other optical source may have a sufficiently fast response time to eliminate the need for an independent modulator. In some embodiments, one or more of the filter elements may provide appropriate modulation. In some uses of the system of FIG. 9C, one or more of the detector systems may be disabled. In some embodiments, Raman detection may occur during a period of irradiation while one or both of fluorescence and phosphorescence detection may occur at one or more times (e.g. in whole or in part, after irradiation has ceased) and fluorescence and/or phosphorescence emission radiation for different wavelengths and different times may be determined. In some embodiments, one or more of the detection methods may be used initially and followed by one or more of the other detection methods. Such follow up detection may be based in whole or in part on a preliminary analysis of the results of the initial detection and may provide confirmation of detected or non-detected substances or may provide further specificity concerning potentially present substances.

Various alternatives to the embodiment of FIG. 9C exists. In one such embodiment, the Raman spectral filter may be used to provide different wavelengths to the Raman detector as the sample is being irradiated while the tunable filters 214-2 and 214-3 could both be used to direct different wavelengths of emission radiation onto detectors 516-2 and 516-3 at the same time for simultaneous fluorescence spectral detection and at a later time for simultaneous phosphorescence detection. In still other embodiments, additional combined fluorescence and phosphorescence filters and detectors may be provided to allow for additional simultaneous spectral detection at different wavelengths.

FIG. 10A provides a block diagram of a chemical analyzer package or instrument according to some embodiments of the invention where the package includes a power supply and a controller.

FIG. 10B provides a block diagram of a chemical analyzer package according to some embodiments of the invention where the package includes an output device while a power supply and/or analyzer may be separate from the package.

Figure 10C:
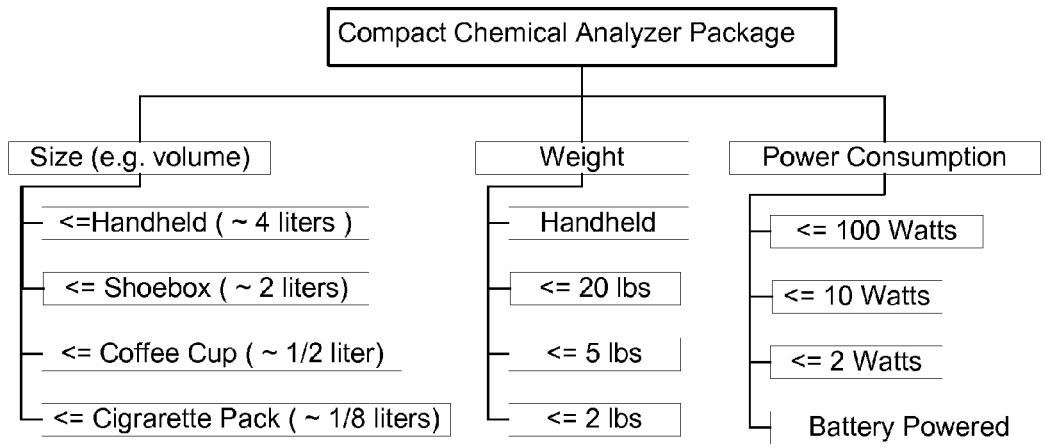
FIG. 10C provides a block diagram illustrating some preferential sizes, weights, and power consumption levels associated with a compact chemical analyzer package according to some embodiments of the invention.

FIG. 10C provides a block diagram illustrating some preferential volumes, weights, and power consumption levels associated with a compact chemical analyzer package according to some embodiments of the invention. Of course in other embodiments, other instruments having other volumes, weight, and power consumption are possible.

Analytical instruments in the context of the present application refer to instruments that analyze a sample of material by exposing that material to a radiation and then detecting selected radiation, current, or voltage resulting from the interaction between the incident radiation and the sample. Some preferred systems also include a computer and appropriate software to aid in the analysis. Sample analytical instruments include Raman spectroscopy systems, UV resonance Raman spectroscopy systems, electrophoresis systems (e.g. gel plane or capillary type), and high performance liquid chromatography systems. The samples to be analyzed may be labeled or non-labeled. The samples may be of DNA or molecular or chemical structures.

Figure 12:
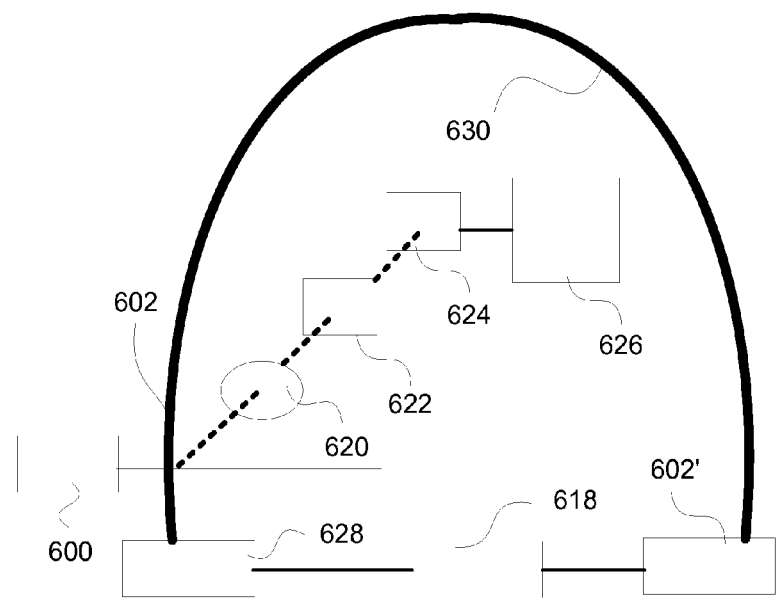
FIG. 12 provides a schematic depiction of an analytic instrument according to some additional embodiments of the invention.

FIG. 12 illustrates the elements of a capillary electrophoresis instrument with a laser induced fluorescence detector. A laser output beam from a laser 600 (e.g. a semiconductor laser or sputtering metal ion hollow cathode laser) is incident on a sample of material 602 inside capillary 630. The sample of material has been separated or segregated from a sample source 602' by the process of electrophoresis and dumped into reservoir 628. Power supply 618 provides the high voltage, low current needed to drive the electrophoretic separation process. The separated material 602 fluoresces when excited by the laser radiation due to absorption by natural or labeling fluorophors within the sample. The fluorescence light is collected by lens 620, passed through filter 622 which blocks Rayleigh scattered light at the laser wavelength, and is collected by detector 624 and processed by computer 626. Variations of this optical detection method might use a semiconductor laser or hollow cathode laser in conjunction with a refractive index detector or Raman spectroscopic detector (including, e.g. a UV tunable filter). The electrophoretic separation can be done in a capillary or in a planar gel, which is in common use. The system may also include one or more wavelength blocking elements (e.g. tunable filters) for separating one or more bands of fluorescence emission wavelengths excited in a sample by the incident radiation.

Figure 13:
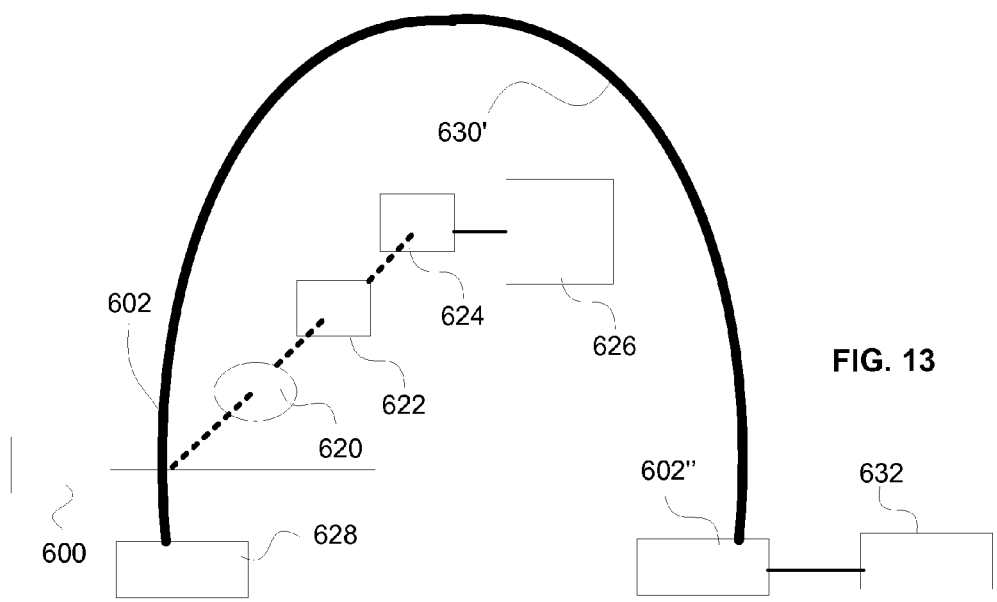
FIG. 13 provides a schematic depiction of an analytic instrument according to some further embodiments of the invention.

FIG. 13 illustrates the elements of a liquid chromatography instrument with a laser induced fluorescence detector. A laser output beam from, e.g. a semiconductor laser or sputtering metal ion hollow cathode laser 600 is incident on a sample of material 602 within capillary 630' which has been separated or segregated from a sample source 602" by the process of liquid chromatography and dumped into reservoir 628. The separation process is driven by pressure supplied by pump 632. The separated material 602 fluoresces when excited by the laser radiation due to absorption in natural or labeling fluorophors within the sample. The fluorescence radiation is collected by lens 620, passed through filter 622 which blocks Rayleigh scattered light at the laser wavelength, is collected by detector 624 and processed by computer 626. Other variations of this optical detection method may use, e.g., a semiconductor laser or sputtering metal ion hollow cathode laser in conjunction with a refractive index detector or Raman spectroscopic detector (e.g. including a tunable filter).

The use of semiconductor lasers (e.g. electron beam pumped semiconductor lasers or sputtering metal ion hollow cathode lasers in the above applications greatly simplifies these types of instruments. Use of tunable filters in combination with these lasers in some embodiments may also result in simplification of analytic instruments, size and weight reductions, improved reliability, and/or decreased power consumption.

This application incorporates herein by reference the teachings of U.S. patent application Ser. No. 11/245,418, filed Oct. 5, 2005 which is entitled "Electron Beam Pumped Semiconductor Laser" and was filed by Hug et al.

In view of the teachings herein, many further embodiments, alternatives in design and uses of the instant invention will be apparent to those of skill in the art. As such, it is not intended that the invention be limited to the particular illustrative embodiments, alternatives, and uses described above but instead that it be solely limited by the claims presented hereafter.

We claim:

1. A method of providing a chemical analysis of a sample, comprising:
   (a) supplying a sample to be analyzed;
   (b) applying ultraviolet excitation radiation from a source directly or indirectly onto the sample to produce emission radiation in the form of Raman emission radiation within a first range of wavelengths and photoluminescence emission radiation within a second range of wavelengths;
   (c) receiving the emission radiation, directly or indirectly, from the sample at at least one first spectral filter which is capable of passing the Raman emission radiation within at least a portion of the first range of wavelengths along a first optical path;
   (d) receiving the emission radiation, directly or indirectly, from the sample at at least one second spectral filter which is capable of passing the photoluminescence emission radiation within at least a portion of the second range of wavelengths along a second optical path;

(e) measuring an amount of the Raman emission radiation using at least one first detector located directly or indirectly along the first optical path;

(f) measuring an amount of the photoluminescence emission radiation using at least one second detector located directly or indirectly along the second optical path; and (g) correlating information concerning the amounts of the Raman emission radiation and photoluminescence emission radiation measured by the at least one first detector and the at least one second detector, respectively, with data associated with one or more chemical compounds of interest to provide at least a partial chemical analysis of the sample.

2. The method of claim 1 wherein the photoluminescence emission radiation comprises fluorescence emission radiation.

3. The method of claim 1 wherein the photoluminescence emission radiation comprises phosphorescence emission radiation.

4. The method of claim 1 wherein the photoluminescence emission radiation comprises both fluorescence and phosphorescence emission radiation which are each measured by the at least one second detector at difference times.

5. The method of claim 1 wherein the source comprises a source selected from the group consisting of: (1) a semiconductor source, (2) a an electron beam pumped semiconductor laser; (3) an electron beam pumped incoherent semiconductor source; and (4) an electron beam pumped AlGaN source; and (5) a hollow cathode laser.

6. The method of claim 1 wherein the excitation radiation has wavelength selected from the group consisting of (1) a wavelength less than 300 nm and (2) a wavelength less than about 250 nm.

7. The method of claim 1 wherein at least one of the at least one first spectral filter or at least one second spectral filter comprises a selected filter chosen from the group consisting of (1) a tunable filter; (2) a dispersive device; (3) an acousto-optic tunable filter; and (4) a temperature tunable filter.

8. The method of claim 5 wherein the chemical analysis is performed in conjunction with one or more sample handling or separation methods selected from the group consisting of: (1) capillary electrophoresis (CE), (2) capillary electrochromatography (CEC), (3) high performance liquid chromatography (HPLC), (4) microcapillary HPLC, (5) flow cytometry, (6) a liquid flow cell methods, (7) an air flow cell methods, and (8) a surface detection method.

9. The method of claim 5 wherein the selected filter comprises an angle tunable filter and the orientation of the angle tunable filter, with respect to received emission radiation, is adjustable so as to enable the Raman emission radiation or the photoluminescence radiation that reaches the at least one first detector or the at least one second detector, respectively, to vary in wavelength.

10. The method of claim 9 wherein the selected filter comprises a tunable filter and wherein the method further comprises repeating the receiving and measuring operations with the at least one tunable filter tuned to different wavelengths so as to obtain a plurality of measurements for a plurality of wavelengths, wherein the correlating comprises determining relative amounts of the measurements for at least two different wavelengths of the plurality of wavelengths and comparing the relative amounts with the data.

11. The method of claim 1 wherein the measuring of the amount of the Raman emission radiation and the measuring of the amount of the photoluminescence emission radiation occur simultaneously.

12. The method of claim 1 wherein the measuring of the amount of the Raman emission radiation and measuring of the amount of the photoluminescence emission radiation occur at different times.

13. The method of claim 1 wherein the measuring of the amount of an emission radiation selected from the group consisting of the Raman emission radiation and the photoluminescence emission radiation is repeated multiple times.

14. The method of claim 13 wherein at least one of the repeated multiple times occurs after irradiation of the sample has ended.

15. A method of providing a chemical analysis of a sample, comprising:

(a) supplying a sample to be analyzed;

(b) applying ultraviolet excitation radiation from a source directly or indirectly onto the sample to produce emission radiation in the form of photoluminescence emission radiation within a first range of wavelengths;

(c) receiving the emission radiation, directly or indirectly, from the sample at at least one first spectral filter which is capable of passing the photoluminescence emission radiation within at least a portion of the first range of wavelengths along a first optical path;

(d) measuring an amount of the photoluminescence emission radiation using at least one first detector located directly or indirectly along the first optical path; and (e) correlating information concerning the amounts of the photoluminescence emission radiation measured by the at least one first detector with data associated with one or more chemical compounds of interest to provide at least a partial chemical analysis of the sample, wherein the source comprises a source selected from the group consisting of: (1) a semiconductor source, (2) a an electron beam pumped semiconductor laser; (3) an electron beam pumped incoherent semiconductor source; and (4) an electron beam pumped AlGaN source; and (5) a hollow cathode laser.

16. The method of claim 15 wherein the photoluminescence emission radiation comprises fluorescence emission radiation.

17. The method of claim 15 wherein the photoluminescence emission radiation comprises phosphorescence emission radiation.

18. The method of claim 15 wherein the photoluminescence emission radiation comprises both fluorescence and phosphorescence emission radiation which are each measured by the at least one first detector at difference times.

19. The method of claim 15 additionally comprising:

(f) receiving photoluminescence emission radiation, directly or indirectly, from the sample at at least one second spectral filter which is capable of passing photoluminescence emission radiation within a second range of wavelengths, which is different from the first range of wavelengths, along a second optical path;

(g) measuring an amount of the photoluminescence emission radiation within the second range of wavelengths using at least one second detector located directly or indirectly along the second optical path;

(h) correlating information concerning the amount of photoluminescence emission radiation within the second range of wavelengths measured by the at least one second detector with data associated with one or more chemical compounds of interest to provide at least partial chemical analysis of the sample.

20. The method of claim 19 wherein the at least portion of the first range of wavelengths corresponds to fluorescence emission radiation and the at least portion of the second range of wavelengths corresponds to phosphorescence emission radiation.

21. The method of claim 15 additionally comprising:
(f) receiving Raman emission radiation, directly or indirectly, from the sample at at least one second spectral filter which is capable of passing Raman emission radiation within a second range of wavelengths, which is different from the first range of wavelengths, along a second optical path;
(g) measuring an amount of the Raman emission radiation within the second range of wavelengths using at least one second detector located directly or indirectly along the second optical path;
(h) correlating information concerning the amount of Raman emission radiation within the second range of wavelengths measured by the at least one second detector with data associated with one or more chemical compounds of interest to provide at least partial chemical analysis of the sample.

22. The method of claim 15 wherein the excitation radiation has wavelength selected from the group consisting of (1) a wavelength less than 300 nm and (2) a wavelength less than about 250 nm.

23. The method of claim 19 wherein at least one of the at least one first spectral filter or at least one second spectral filter comprises a selected filter chosen from the group consisting of (1) a tunable filter; (2) a dispersive device; (3) an acousto-optic tunable filter; and (4) a temperature tunable filter.

24. The method of claim 15 wherein the chemical analysis is performed in conjunction with one or more sample handling or separation methods selected from the group consisting of: (1) capillary electrophoresis (CE), (2) capillary electrochromatography (CEC), (3) high performance liquid chromatography (HPLC), (4) microcapillary HPLC, (5) flow cytometry, (6) a liquid flow cell methods, (7) an air flow cell methods, and (8) a surface detection method.

25. The method of claim 15 wherein a selected one of the at least one first spectral filter comprises at least one angle tunable filter and the orientation of the at least one angle tunable filter, with respect to received emission radiation, is adjustable so as to enable the photoluminescence emission radiation that reaches the selected one of the at least one first detector to vary in wavelength.

26. The method of claim 25 wherein the method further comprises repeating the receiving and measuring operations with the at least one tunable filter tuned to different wavelengths so as to obtain a plurality of measurements for a plurality of wavelengths, wherein the correlating comprises determining relative amounts of the measurements for at least two different wavelengths of the plurality of wavelengths and comparing the relative amounts with the data.

27. The method of claim 15 wherein the measuring of the amount of photoluminescence emission radiation using the at least one first detector is repeated multiple times after the irradiation of the sample has ended.

28. The method of claim 27 wherein the photoluminescence emission radiation comprises phosphorescence emission radiation and wherein the correlation of information comprises the use of measured phosphorescence emission radiation from a plurality of different times after irradiation of the sample has ended.

29. The method of claim 27 wherein the photoluminescence emission radiation comprises fluorescence emission radiation and wherein the correlation of information comprises the use of measured fluorescence emission radiation from a plurality of different times after irradiation of the sample has ended.

* * * * *

UNITED STATES PATENT AND TRADEMARK OFFICE
CERTIFICATE OF CORRECTION

PATENT NO.        : 8,395,770 B1
APPLICATION NO.   : 12/545772
DATED             : March 12, 2013
INVENTOR(S)       : William F. Hug, Ray D. Reid and Rohit Bhartia It is certified that error appears in the above-identified patent and that said Letters Patent is hereby corrected as shown below:

In the Specification

On Column 1, lines 17 - 19,
delete,
"The inventions set forth herein were made with U.S. Government support under NASA Contract No. NAS2-02086 and/or under DARPA Contract No. W31P4Q-04-C-RO39." and
add
-- The inventions set forth herein were made with U.S. Government support under NASA Contract No. NAS2-02086, and/or under DARPA Contract No. W31P4Q-04-C-RO39, and/or under DTRA Contract No. HDTRA1-09-C-0010. --.

Signed and Sealed this
First Day of March, 2016

Michelle K. Lee
*Director of the United States Patent and Trademark Office*